(12) United States Patent
Poslavsky et al.

(10) Patent No.: US 7,321,426 B1
(45) Date of Patent: Jan. 22, 2008

(54) OPTICAL METROLOGY ON PATTERNED SAMPLES

(75) Inventors: Leonid Poslavsky, Belmont, CA (US); Carlos L. Ygartua, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 418 days.

(21) Appl. No.: 10/859,637

(22) Filed: Jun. 2, 2004

(51) Int. Cl.
*G01J 4/00* (2006.01)
*G01B 11/00* (2006.01)

(52) U.S. Cl. ...................................... 356/369; 356/401
(58) Field of Classification Search ................ 356/369, 356/401; 430/22
See application file for complete search history.

(56) References Cited

U.S. PATENT DOCUMENTS

| | | | |
|---|---|---|---|
| 6,102,775 A * | 8/2000 | Ushio et al. ................... 451/6 |
| 6,408,677 B1 * | 6/2002 | Suzuki ....................... 73/1.89 |
| 6,484,064 B1 * | 11/2002 | Campbell ................... 700/100 |
| 6,657,736 B1 * | 12/2003 | Finarov et al. ............ 356/625 |
| 6,699,627 B2 * | 3/2004 | Smith et al. .................. 430/22 |
| 6,819,426 B2 * | 11/2004 | Sezginer et al. ............ 356/401 |
| 7,054,007 B2 * | 5/2006 | Leroux et al. .............. 356/401 |
| 2006/0098195 A1 * | 5/2006 | Brill et al. .................. 356/326 |

OTHER PUBLICATIONS

Moharam et al.: "Formulation For Stable And Efficient Implementation Of The Rigorous Coupled-Wave Analysis Of Binary Gratings", J. Opt. Soc. Am. A/vol. 12, No. 5/May 1995, pp. 1068-1076.

* cited by examiner

*Primary Examiner*—Gregory J. Toatley, Jr.
*Assistant Examiner*—Jarreas Underwood
(74) *Attorney, Agent, or Firm*—Bever, Hoffman & Harms, LLP; Jeanette S. Harms

(57) ABSTRACT

An optical metrology system includes model approximation logic for generating an optical model based on experimental data. By eliminating theoretical model generation, in which the fundamental equations of a test sample must be solved, the model approximation logic significantly reduces the computational requirements of the metrology system when measuring films formed on patterned base layers. The experimental model can be created by selecting an expected mathematical form for the final model, gathering experimental data, and compiling a lookup model. The lookup model can include the actual measurement data sorted by output (attribute) value, or can include "grating factors" that represent compensation factors that, when applied to standard monolithic model equations, compensate for the optical effects of grating layers.

42 Claims, 21 Drawing Sheets

OPTICAL METROLOGY ON PATTERNED SAMPLES

BACKGROUND OF THE INVENTION

1. Field of the Invention

The invention relates to the field of metrology, and in particular to computationally efficient optical metrology systems.

2. Related Art

Optical metrology tools (such as ellipsometry tools or reflectometry tools) determine the attributes of thin films in integrated circuits (ICs) by reflecting a probe beam of light off of the thin films. Data measurements from the reflected beam are collected and compared to an optical model of the thin films and any interfacing structures to generate values for the thin film attribute(s) of interest.

Typically, optical metrology is performed on thin films formed on predetermined target regions of a wafer. Those target regions have historically included thin films formed on uniform (monolithic) base layers. However, as device geometries decrease and IC yield and performance requirements become more sensitive to process defects, monolithic targets (i.e., targets located over monolithic base layers) may not be sufficiently representative of the actual thin film characteristics in the active regions of the IC.

Therefore, modern ICs sometimes incorporate "patterned targets", i.e., targets located over patterned (non-monolithic) base layers. Typically, a patterned base layer is a grating base layer that can include periodic structures (e.g., lines), which can be formed from metal, silicon, or any other material used in an IC. A patterned base layer allows a metrology operation to be performed on a thin film that more closely resembles the physical, chemical, and mechanical properties of thin film portions in the active device area of the wafer.

Furthermore, as device geometries become smaller, the large planar areas of metal (20-30 um square, which is large compared to transistors) in the base layers of conventional monolithic targets can become problematic. Specifically, such large planar areas of metal can be difficult to accurately produce. For example, chemical-mechanical polishing (CMP) can lead to unacceptable "dishing" as the soft metal (relative to semiconductor and oxide materials) deforms under the CMP slurry load. This dishing can significantly affect the accuracy of any optical metrology techniques used in the region. The softer the metal, the more this problem is amplified, and the more measurement accuracy is degraded. Since a large proportion of a patterned base layer is formed from semiconductor materials (i.e., the metal lines are typically formed in an oxide layer), it is less susceptible to dishing.

Therefore, the use of grating targets can beneficially enhance the quality of optical metrology. Conventional methods for performing optical metrology on grating targets typically involve the same methodology used for metrology on monolithic targets. Specifically, a theoretical model (i.e., a set of equations based upon fundamental optical principles) is created for the grating target. The theoretical model is then used to determine values for the thin film "attribute of interest" (AOI, the thin film attribute for which an output value is desired). This process is described in greater detail with respect to FIGS. 1A-1D.

In FIG. 1A, a theoretical model C(TH) is generated for the test sample. This model can be created by, for example, solving the fundamental Fresnel equations that define the behavior of the probe beam at the test sample. Then, in FIG. 1B, measurement data D(MEAS) for the test sample is collected (often across a range of wavelengths or across a range of incident angles for ellipsometry or reflectometry). Measurement data D(MEAS) can be any ellipsometry measurement parameter, such as $\alpha$, $\beta$, $\Psi$, or $\Delta$, or any reflectometry measurement parameter, such as reflectivity ($\mathcal{R}$).

Next, in FIG. 1C, theoretical model C(TH) is regressed along the AOIs until the difference (error) between the curves for theoretical model C(TH) and measurement data D(MEAS) is below some threshold limit. For example, if thickness is the AOI being determined by the metrology process, appropriate values would be assigned to the other thin film attributes in the theoretical model (e.g., index of refraction, extinction coefficient, material composition), and the thickness value would be varied until the regressed data (curve C(RE)) matched the measured data (curve D(MEAS)), as shown in FIG. 1D. The thickness value at this point could then be output as the thickness of the thin film layer.

This sequence of operations depicted in FIGS. 1A-1D is summarized in the flow diagram of FIG. 1E. Thus, in a "DEFINE FUNDAMENTAL EQUATIONS" step 110, a set of equations that define the behavior of the probe beam at the test sample (e.g., Fresnel equations) are specified. Then, in a "GENERATE THEORETICAL MODEL" step 120, the fundamental equations defined in step 110 are solved to create a theoretical model for the test sample. Steps 110 and 120 therefore correspond to FIG. 1A.

Next, in a "COLLECT MEASUREMENT DATA" step 130, the reflected probe beam data is gathered, as shown in FIG. 1B. The theoretical model is then regressed along the AOI(s) to match the measured data in a "REGRESS MODEL EQUATIONS" step 140. Finally, in an "OUTPUT AOI VALUE(S)" step 150, a value(s) for the AOI(s) of the thin film layer is derived from the regressed model equations.

In this manner, conventional optical metrology systems are able to calculate values for thin film attributes by using a rigorous model of the thin film stack (i.e., the thin film and any underlying layers). Unfortunately, the computational power required to generate the theoretical optical model for a grating-based thin film stack (i.e., a thin film(s) formed over a grating) can be excessive, due to the sheer complexity of the equations that describe the optical behavior of such structures.

For example, an ellipsometry tool measures the ellipsometric angles $\psi$ and $\Delta$, where $\tan(\psi)$ is the relative amplitude ratio of the incident and reflected probe beams, while $\Delta$ is the relative phase shift between the incident and reflected probe beams. Ellipsometric angles $\psi$ and $\Delta$ are related to the complex ratio of the Fresnel reflection coefficients Rp and Rs for light polarized parallel (p) and perpendicular (s) to the plane of incidence by the following equation:

$$\tan(\psi)e^{i\Delta} = R_p/R_s \qquad [1]$$

where $R_p$ and $R_s$ are the complex Fresnel reflection coefficients at the surface of the film stack for light polarized parallel and perpendicular, respectively, to the plane of incidence.

Fresnel reflection coefficients $R_p$ and $R_s$ are complex functions of the wavelength(s) and angle(s) of incidence of the probe beam, and also of the optical constants (e.g., index of refraction, extinction coefficient) of the materials in the film stack. Specific functions for Fresnel reflection coefficients Rp and $R_s$ can be defined as sets of model equations that are associated with the individual layers making up the film stack.

For example, the reflectivity at the bottom of a layer (just above the top of the layer below) can be expressed as a function of the interface Fresnel reflectance and the effective reflectivity at the top of the layer immediately below the layer of interest, as indicated by the following equation:

$$R_B(j) = (R_F(j) + R_T(j-1))/(1 + R_F(j)*R_T(j-1))  \quad [2]$$

where $R_B(j)$ is the reflectance at the bottom of layer j ("lower reflectance"), $R_F(j)$ is the interface Fresnel reflectance between layer j and layer j−1 (i.e., the layer immediately below layer j), and $R_T(j-1)$ is the reflectance at the top of layer j−1 ("upper reflectance").

Upper reflectance $R_T(j-1)$ can be given by the following:

$$R_T(j-1) = R_B(j-1) \exp(-4\pi i^{(n(j-1)d(j-1)\cos(\theta(j-1))/\lambda)})  \quad [3]$$

where $R_B(j-1)$ is the lower reflectance of layer j−1, n(j−1) is the index of refraction of layer j−1, d(j−1) is the thickness of layer j−1, and θ(j−1) is the angle of incidence of the probe beam as it enters layer j−1.

Index of refraction $n_j$, can be represented by the Cauchy equation:

$$n(j-1) = A(j-1) + B(j-1)/\lambda^2 + C(j-1)/\lambda^4  \quad [4]$$

where A(j−1), B(j−1), and C(j−1) are Cauchy coefficients for index of refraction that depend on the material properties of layer j−1 and the wavelength λ of the probe beam. Note that various other equations can be used to define index of refraction.

Note further that depending on the properties of the various material layers, index of refraction n(j−1) may need to be replaced with the more accurate "complex index of refraction" N(j−1), which has both real and imaginary portions, as indicated below:

$$N(j-1) = n(j-1) + ik(j-1)  \quad [5]$$

where k(j−1) is the extinction coefficient for the appropriate material layer given by:

$$k(j-1) = D(j-1) + E(j-1)/\lambda^2 + F(j-1)/\lambda^4  \quad [6]$$

where D(j−1), E(j−1), and F(j−1) are Cauchy coefficients for extinction that depend on the material properties of layer j−1 and the wavelength λ of the probe beam.

Meanwhile, interface Fresnel reflectance $R_F(j)$ is given by the following:

$$R_F(j) = (p(j) - p(j-1))/(p(j) + p(j-1))  \quad [7]$$

where p(j) and p(j−1) represent dispersion factors for layers j and j−1, respectively. For light polarized in the parallel direction (i.e., the direction parallel to the plane of incidence), dispersion factor p(j) is given by the following:

$$p(j) = n(j)\cos(\theta(j))  \quad [8]$$

where n(j) is the index of refraction of layer j, and θ(j) is the angle of incidence of the probe beam as it enters layer j. For light polarized in the in the perpendicular direction (i.e., perpendicular to the plane of incidence), dispersion factor p(j) is given by the following:

$$p(j) = \cos(\theta(j))/n(j)  \quad [9]$$

Dispersion factor p(j−1) for is calculated in a similar manner for the two light polarizations.

Equation 2 can be used to define a lower reflectance equation for each layer of the film stack. This results in a first set of reflectance equations for light polarized in the parallel direction (based on Equations 2 through 8) and a second set of reflectance equations for light polarized in the perpendicular direction (based on Equations 2 through 7 and 9). Within the first and second sets of reflectance equations, if the ambient environment is defined as the topmost "layer" in the film stack, the lower reflectance equation for that ambient layer is equivalent to Fresnel reflection coefficients Rp and Rs, respectively. Therefore, by solving the first and second recursive sets of reflectance equations, the model equations for the film stack can be fully defined.

Note that because the lower reflectance of a given layer is a function of the upper reflectance of the layer below that given layer, each of the two sets of reflectance equations is a recursive set. Note further that the reflectance at the substrate is defined to be zero, which provides a starting point from which both sets of recursive reflectance equations can be solved.

Clearly, the more layers present in the film stack, the more complex the model equation determination becomes. Even so, processing the model equations for a large multi-layer film stack formed on a monolithic base layer can still be performed using reasonable computational power.

However, the incorporation of a patterned base layer under the thin film(s) complicates the Fresnel equations by several orders of magnitude, since the grating structure introduces a large number of additional material interfaces. Each of these new interfaces has its own reflection and refraction effects, and requires additional description (equations). A sample formal derivation of Maxwell's equations for a thin film on a patterned base layer is described in "Formulation for Stable and Efficient Implementation of the Rigorous Coupled-Wave Analysis of Binary Gratings", M. G. Moharam et al., J. Opt. Soc. Am. A, Vol. 12, pp. 1068-1076 (1995), herein incorporated by reference.

Solving the immensely larger set of equations for a grating target is significantly more difficult than solving the equations for a monolithic target and can require on the order of ten thousand times the computing resources required to solve the monolithic target equations. Therefore, metrology systems that use conventional processing techniques to analyze grating targets can be expensive, cumbersome, and slow, due to the sheer volume of computing resources required (both hardware and software resources).

Various approaches have been considered in an effort to reduce some of the computational load placed on metrology systems when analyzing grating targets. For example, the patterned base layer can be treated as a solid layer, thereby simplifying the model equations. The model equations could also be simplified by ignoring phase information and only using reflected intensity data in the calculations. However, in either case, the approximations can result in unacceptable inaccuracy in the final measurement values.

Accordingly, it is desirable to provide a computationally efficient method and system for accurately measuring thin films formed on patterned base layers.

SUMMARY OF THE INVENTION

The invention provides a system and method for accurately measuring attributes (e.g., thickness, index of refraction, coefficient of extinction, surface roughness, composition) of a thin film(s) formed on a patterned base layer by creating an empirical optical model for the test sample. By incorporating the empirical model into an optical metrology measurement technique, the invention beneficially eliminates the need for the complex and resource-intensive computation of accurate theoretical models of the film stack.

The invention applies to any optical metrology tool that can be used to measure one or more thin films formed on a patterned structure, including reflectometry tools (which measure/detect changes in reflected intensity) and ellipsometry tools (which measure/detect changes in reflected intensity and phase). The optical metrology tool can make measurements at a single angle of incidence and/or wavelength, or can make measurements at multiple angles of incidence and/or wavelengths.

According to an embodiment of the invention, the empirical model can be created by selecting an expected model equation form (i.e., a specified set of terms and coefficients), and then regressing the coefficients of that expected form until outputs are generated that adequately match a set of experimental data. This reduces the computing requirements for the metrology system, since computing coefficients for this empirical (mathematical) model from experimental data for a grating target is much less computationally intensive than generating a theoretical model by solving a set of equations for the same grating target.

Note that the coefficients of the expected model form will typically be functions of wavelength and/or angle of incidence. Therefore, at every wavelength and/or angle of incidence, a new set of coefficients will be determined. However, the computational cost of generating these multiple sets of coefficients is still orders of magnitude less than the computational cost of actually solving the theoretical equations for a grating-based thin film stack. Note further that different model equations can be provided for different expected attribute ranges to improve the accuracy of the output values.

According to another embodiment of the invention, the empirical optical model can be generated by compiling sets of data taken at various values of the attribute(s) of interest. For example, reflectivity measurements could be taken from a number of different grating targets having different thin film thicknesses (i.e., thickness is the attribute of interest). These measurements could then be compiled into an empirical lookup model. By interpolating the data in the empirical lookup model to match measured data from a test sample, an output value for the attribute of interest can be generated.

Creation of this type of lookup model is significantly less computationally intensive than generation of a theoretical model. According to another embodiment of the invention, an empirical model can be used to generate these sets of data used in the creation of a lookup model.

According to another embodiment of the invention, the empirical optical model can be generated by compiling sets of grating factor values that, when applied to the standard monolithic base layer model equations, compensate for the optical effects of the grating base layer. By interpolating the grating factor values until the (adjusted) model output matches data from a test sample, an output value for the attribute of interest of the test sample can be generated.

The present invention will be more fully understood in view of the following description and drawings.

DETAILED DESCRIPTION

Figure 1A:
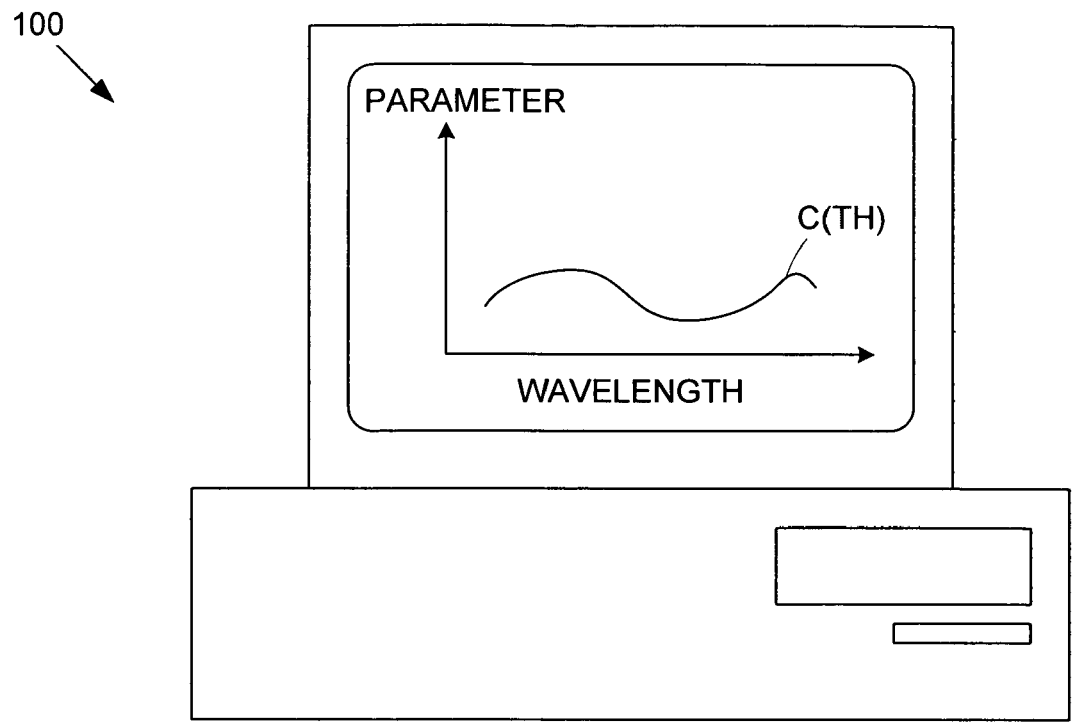
FIGS. 1A-1D are stages in a conventional method for measuring attributes for a thin film formed on a grating.
Figure 1B:
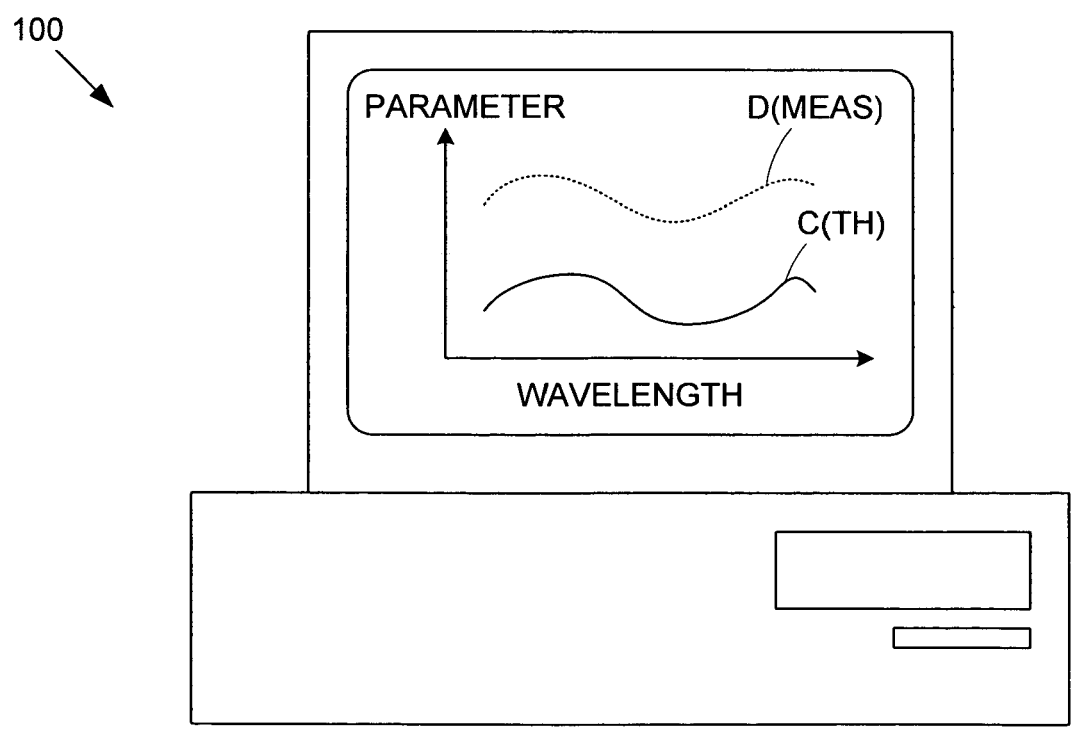
Figure 1C:
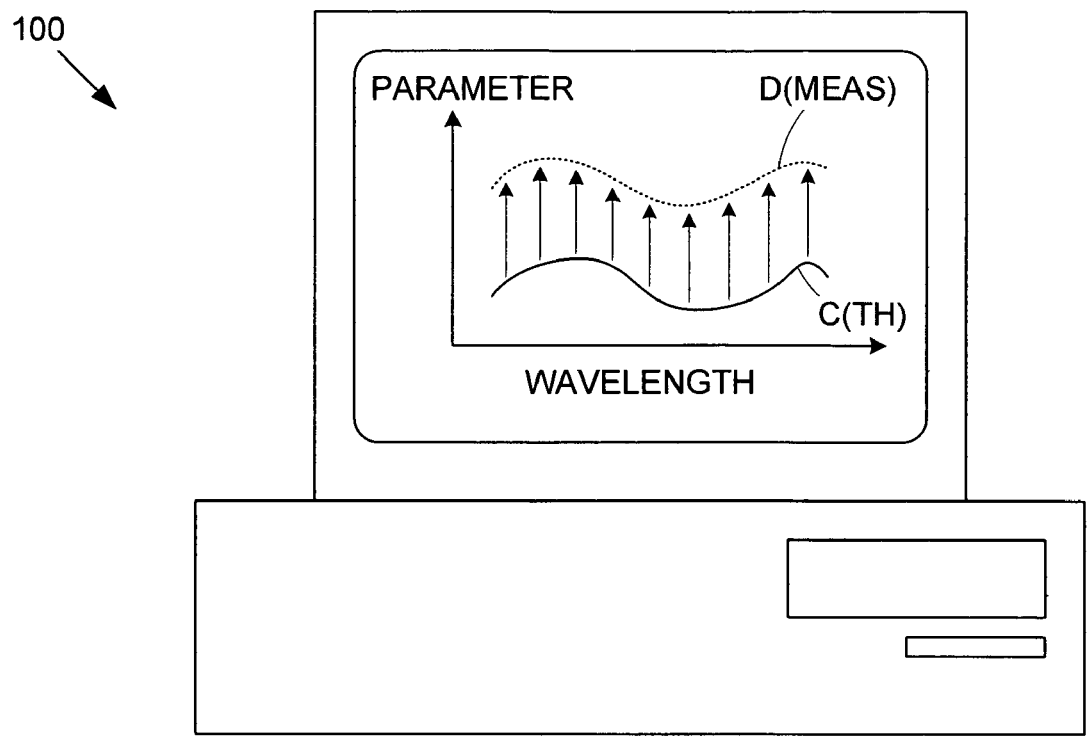
Figure 1D:
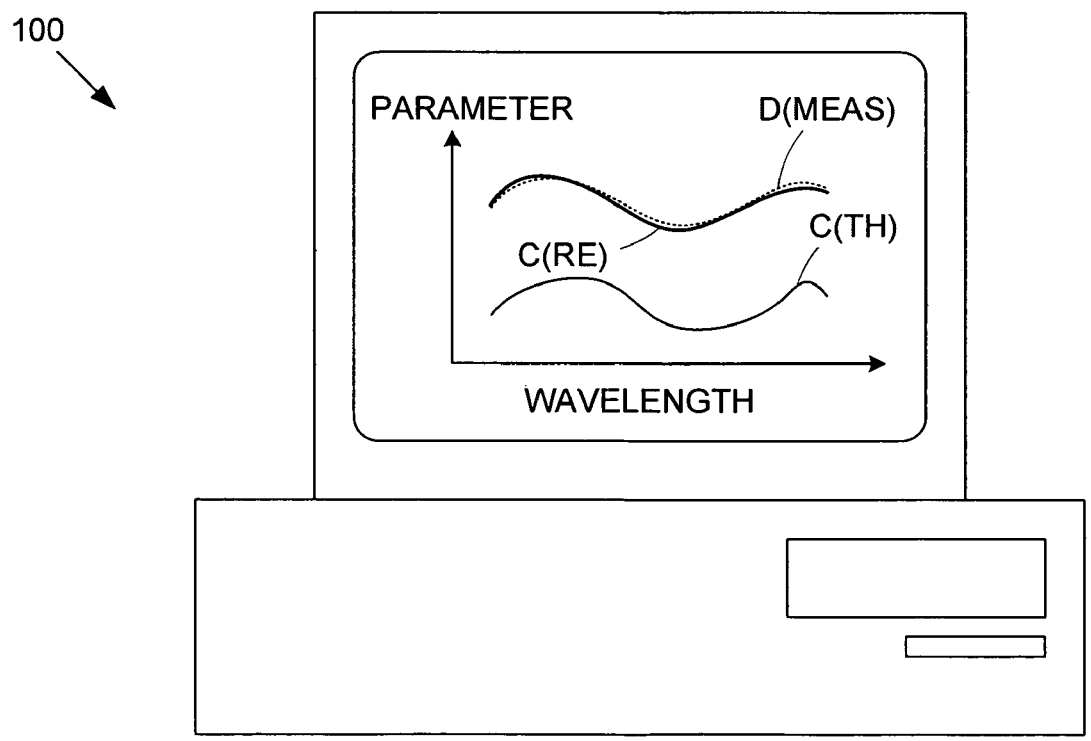
Figure 1E:
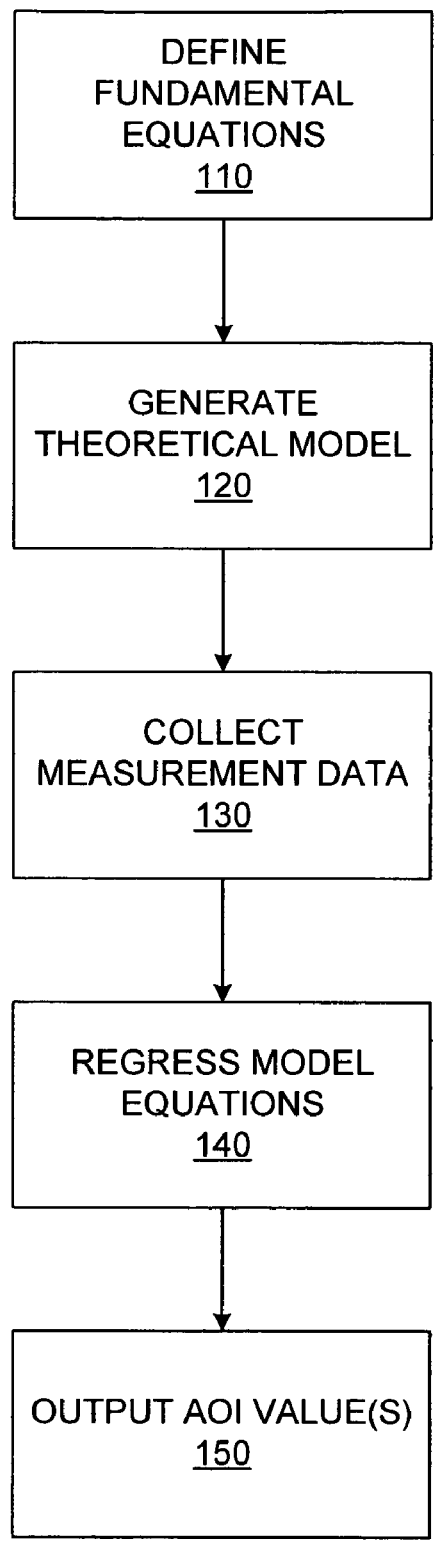
FIG. 1E is a flow diagram of a conventional method for measuring attributes for a thin film formed on a grating.
Figure 2:
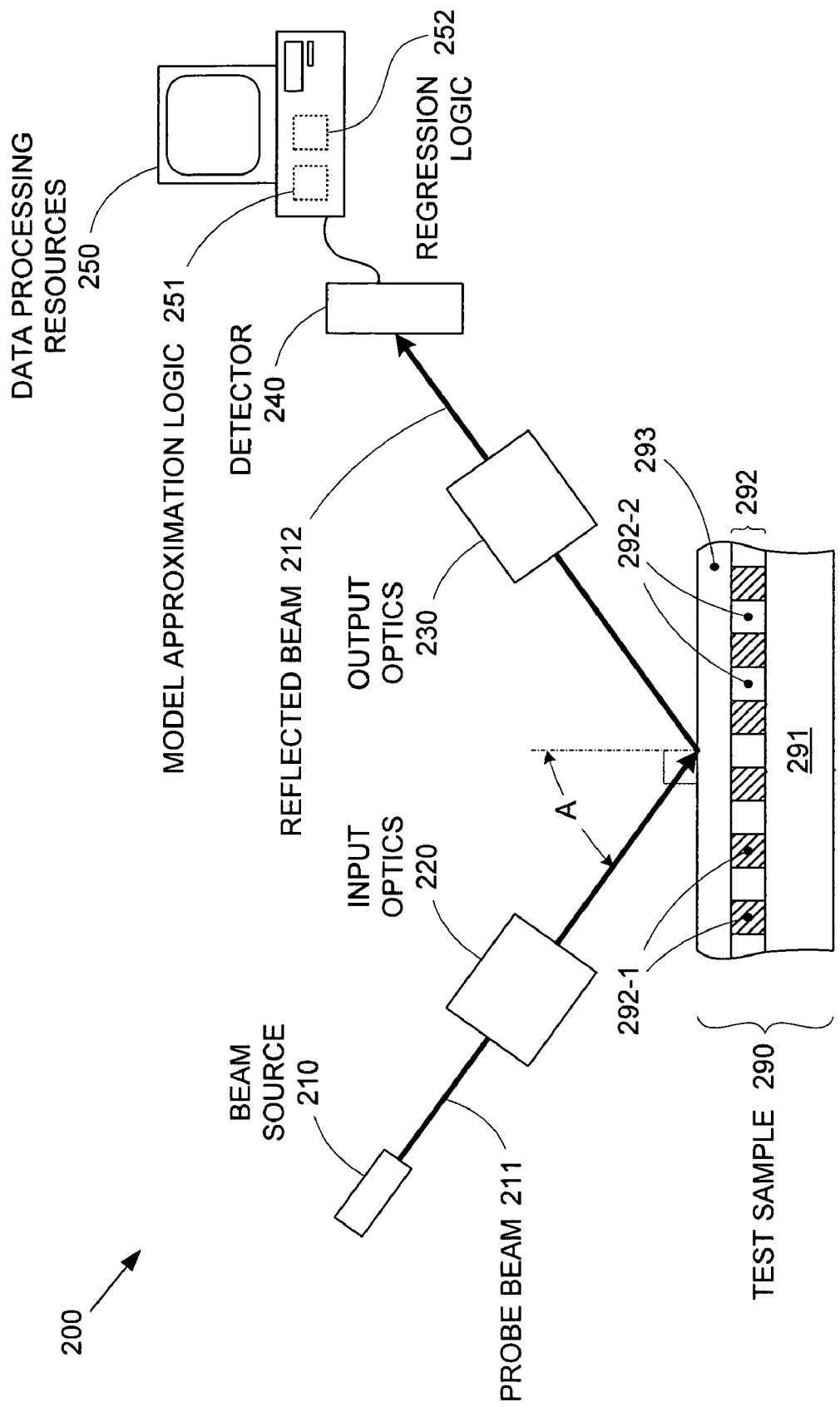
FIG. 2 is a schematic diagram of an optical measurement system that includes model approximation logic, according to an embodiment of the invention.

FIG. 2 shows an optical metrology system 200 for determining values for one or more AOIs (i.e., attributes of interest, such as thickness, index of refraction, roughness, and composition, among others) of a test sample 290, according to an embodiment of the invention. Optical metrology system 200 includes a beam source 210, input optics 220, output optics 230, a detector 240, and data processing resources 250. For exemplary purposes, test sample 290 includes a patterned base layer 292 formed on a substrate 291, and a thin film 293 formed on patterned base layer 292. Patterned base layer 292 includes a series of lines 292-1 (e.g., metal lines) formed in a base material 292-2. Note that while patterned base layer 292 is depicted as a patterned base layer for exemplary purposes, patterned base layer 292 can include any type of patterning. Note further that thin film 293 can be made up of any number of material layers.

To perform a measurement operation, a probe beam 211 generated by beam source 210 is directed onto thin film 293 by input optics 220. A resulting reflected beam 212 is directed by output optics 230 onto detector 240, and the measurements taken by detector 240 are processed by data processing resources 250 to determine values for the desired parameters of thin film 293 (e.g., thickness, index of refraction, or composition). Note that beam source 210, input optics 220, output optics 230, and detector 240 can comprise any types of components that are appropriate for the particular metrology technique employed by optical metrology system 200.

For example, to perform ellipsometry, beam source 210 could comprise a laser or arc lamp, input optics 220 could comprise a polarizer, monochromator, compensator, and/or focusing optics, output optics 230 could comprise a polarizer, analyzer, and/or focusing optics, and detector 240 could comprise a photodiode or charge-coupled device (CCD) array.

Alternatively, to perform reflectometry, beam source 210 could comprise a halogen or deuterium lamp, input optics 220 could comprise a beamsplitter, monochromator, and/or focusing optics, output optics 230 could comprise a prism, diffraction patterned, and/or focusing optics, and detector 240 could comprise a camera or CCD/photodiode array. Various other component combinations will be readily apparent.

To efficiently address the computational complexity introduced by patterned base layer 292 in test sample 290, data processing resources 250 includes model approximation logic 251 (i.e., empirical model generation logic) and regression logic 252. Model approximation logic 251 creates an empirical optical model of the thin film stack using experimental data. Unlike a theoretical model, which is based on general physical laws, an empirical model is at least in part based on experimental or observed data. Therefore, an empirical model can be created without solving the complex set of equations required for a theoretical model, thereby minimizing the computing power requirements of data processing resources 250.

Figure 3:
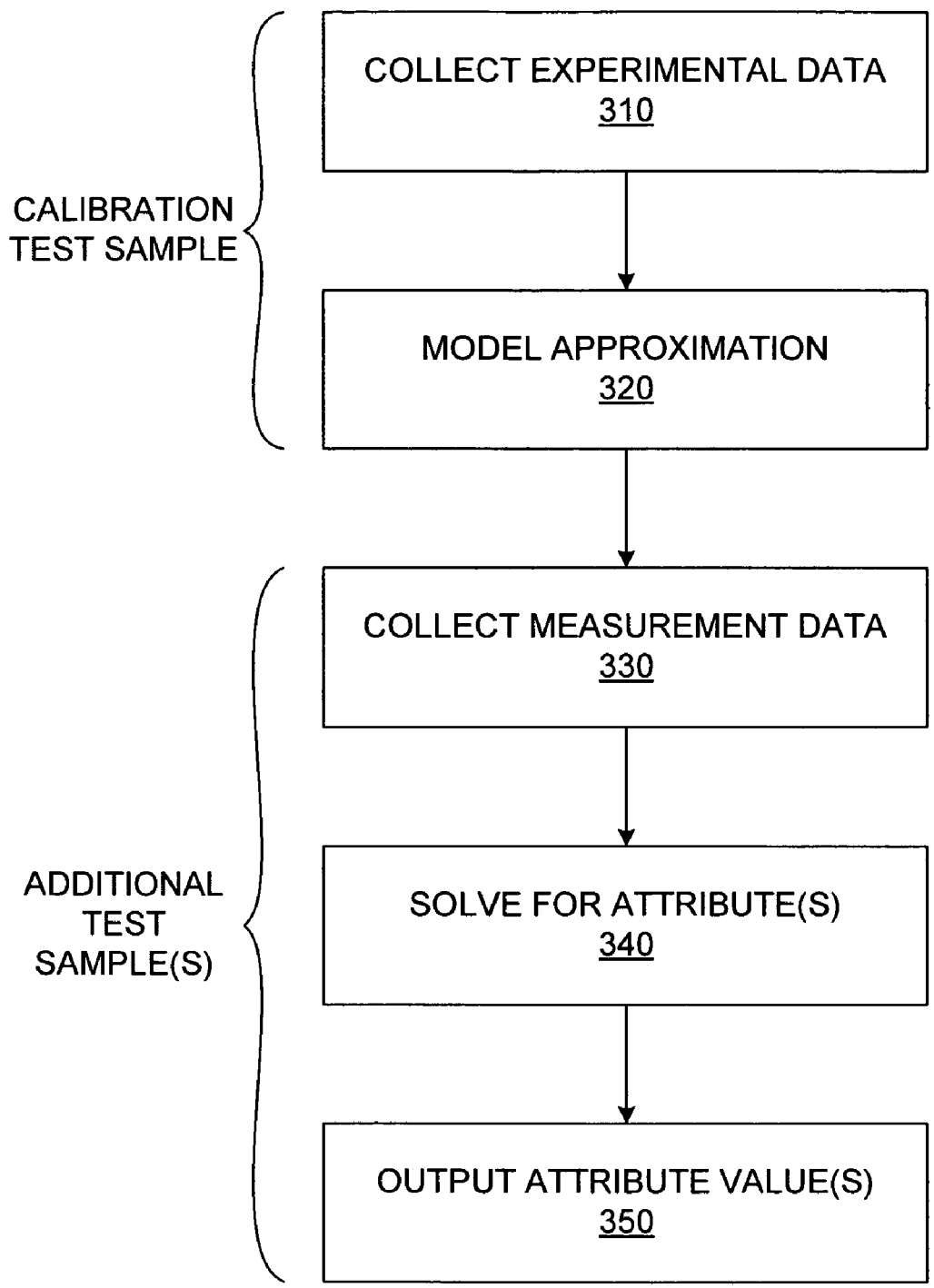
FIG. 3 is a flow diagram of a method for determining thin film attributes using an empirical model, according to an embodiment of the invention.

FIG. 3 shows a flow diagram for an optical metrology operation incorporating an empirical model, in accordance with an embodiment of the invention. In a "COLLECT EXPERIMENTAL DATA" step 310, experimental data (e.g., optical metrology measurement data such as ellipsometric angles tan(Ψ) and Δ, or reflectance $\mathcal{R}$) from one or more calibration test samples is gathered. This experimental data is taken from a target location on the calibration sample that includes a thin film over a patterned base layer (e.g., thin film 293 and patterned base layer 292 shown in FIG. 2). The experimental data is then used to generate an empirical model in a "MODEL APPROXIMATION" step 320.

Note that the term "data" (e.g., experimental data, measurement data) can refer either to standard metrology data types such as ellipsometric angles tan(Ψ) and Δ, or reflectance R, or to the raw data from the measurement tool (e.g., CCD counts or other electrical signals). The invention can be applied to any type of data. Because all metrology tools perform processing operations on metrology data types (conversion from raw data to metrology data is performed immediately by the metrology tool), the exemplary descriptions presented herein are described with respect to metrology data types, rather than raw data types.

To generate the empirical model, the expected value(s) of the AOI(s) (along with the other thin film attribute values) must either be reasonably well known, or else must be explicitly measured. For example, if thickness is the AOI to be determined using the empirical model, the thickness of thin film 293 must be a defined value during "MODEL APPROXIMATION" step 320. In some cases, the process used to form thin film 293 will be well characterized enough that an expected thickness value for thin film 293 will provide sufficient accuracy to generate the empirical model.

However, for improved accuracy, it can be desirable to actually measure the thin film thickness. This measured thickness can be determined by applying conventional optical metrology techniques to one or more monolithic targets that are located on the same test sample as the patterned target(s). The closer the monolithic targets are to the patterned targets, the more closely the measured thin film thickness at the monolithic targets will match the thin film thicknesses at the patterned targets.

Figure 4:
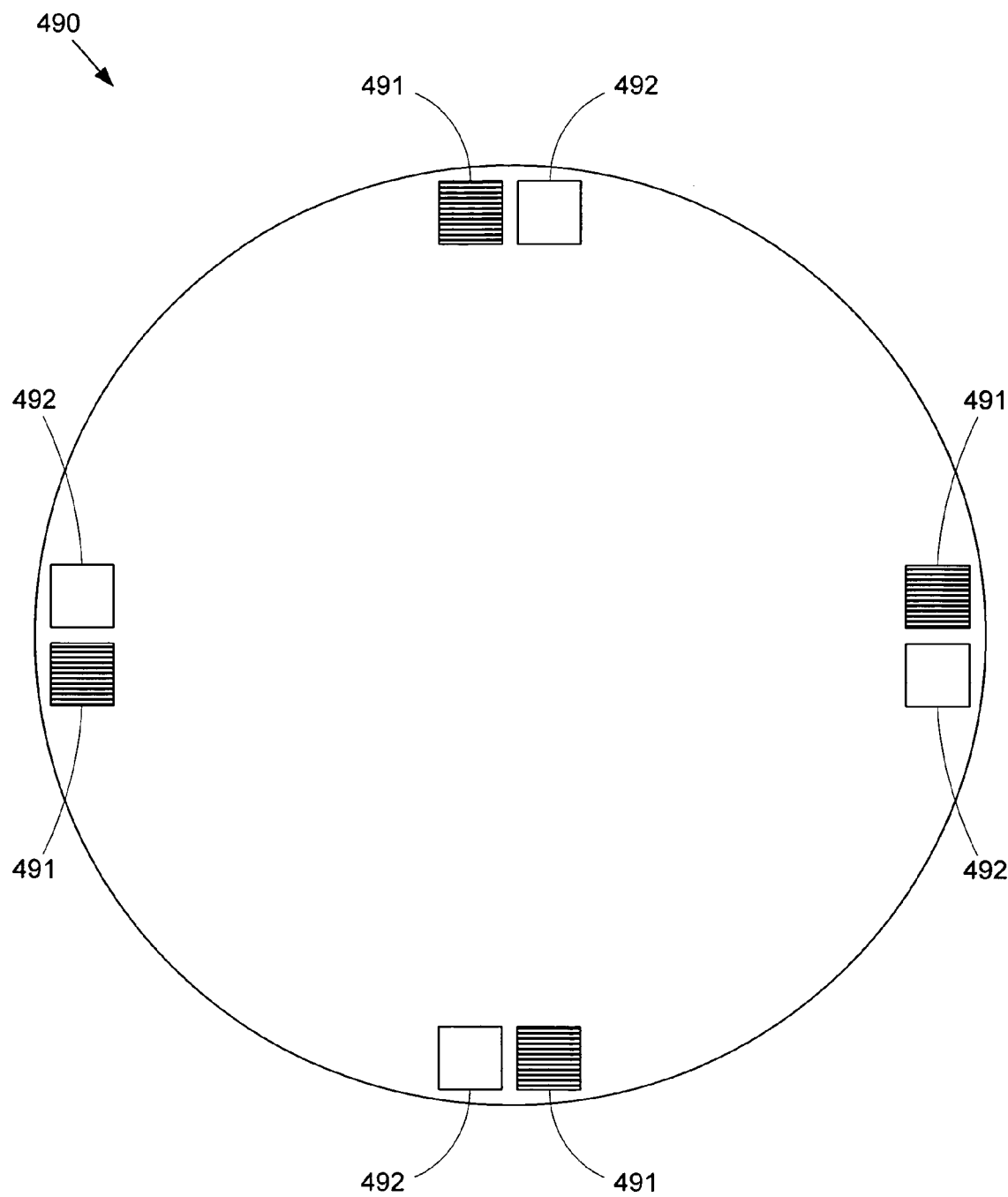
FIG. 4 is a wafer that includes both grating targets and monolithic targets, according to an embodiment of the invention.

FIG. 4 shows a wafer (calibration sample) 490 in accordance with an embodiment of the invention. Wafer 490 includes multiple patterned targets 491 and multiple monolithic targets 492, with each monolithic target 492 being located in close proximity to a patterned target 491. Therefore, the thin film attribute(s) measured at the monolithic targets 492 using conventional metrology techniques can be used when generating the empirical model(s) for the patterned-based targets. Note that while four patterned targets 491 and four monolithic targets 492 are shown in FIG. 4 for exemplary purposes, a wafer in accordance with the invention can include any number patterned and monolithic targets in any arrangement.

Returning to FIG. 3, the expected/measured value(s) of the AOI(s) are used in conjunction with the experimental data to generate an empirical model of the patterned target location. This empirical model can be either a mathematical model (set of equations) or a lookup model (an indexed set of data, equations, or grating factors), both of which are described in greater detail below. In either case, the complex theoretical modeling of the patterned target location is avoided, thereby greatly simplifying model generation.

The empirical model can then be used to determine values for the AOIs of test samples, so long as the base layer(s) at the patterned target(s) of the test sample(s) is substantially similar to the patterned base layer(s) of the calibration sample(s) used to generate the empirical model. In a "COLLECT MEASUREMENT DATA" step 330, measurements are taken at the patterned targets of a test sample(s) to be measured.

Then, in a "SOLVE FOR ATTRIBUTE(S)" step 340, the empirical model generated in step 320 is fitted to the measurement data, i.e., the empirical model is either regressed or interpolated along the AOI(s) until the output of the empirical model matches the measurement data. Note that the "matching" of the empirical model output and the measurement data is based on a predetermined error threshold (tolerance band) that defines a desired degree of correlation between the regressed model and the measurement data.

Finally, in an "OUTPUT ATTRIBUTE VALUE(S)" step 350, the attribute value(s) determined during step 340 are output as the calculated value(s) for the AOI(s). To perform additional measurements on additional test samples, the process can then loop back to step 330.

Figure 5:
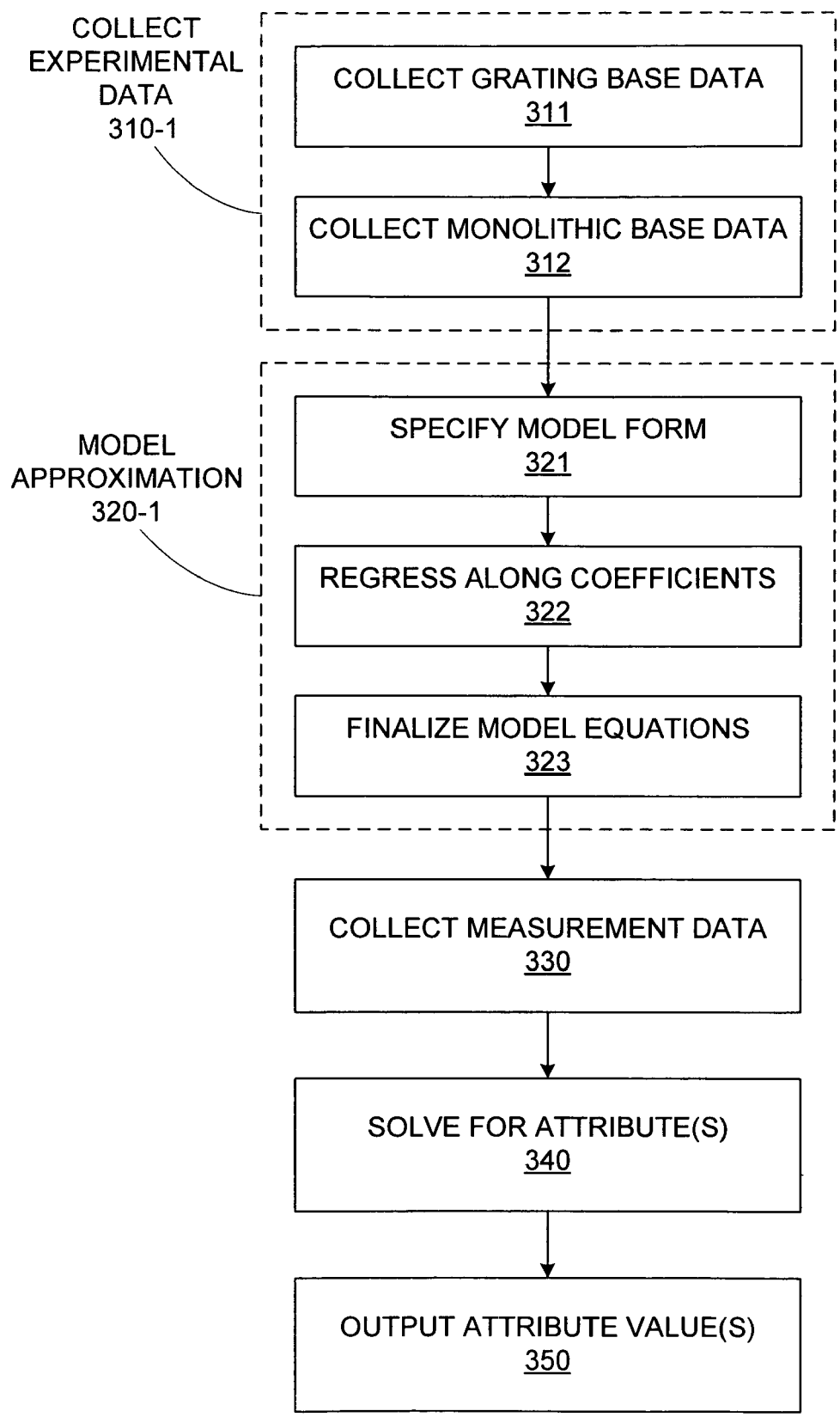
FIG. 5 is a flow diagram of a method for determining thin film attribute values using an empirical model, according to an embodiment of the invention.

FIG. 5 shows a detailed embodiment of the flow chart of FIG. 3, including sub-steps specific to the use of an experimental empirical model, according to an embodiment of the invention. "COLLECT EXPERIMENTAL DATA" step 310-1 (corresponding to step 310 in FIG. 3) begins with a "COLLECT PATTERNED BASE DATA" step 311 in which experimental data is gathered from one or more patterned targets. Measurements can then be taken at one or more monolithic targets (e.g., monolithic targets 492 in FIG. 4) in an optional "COLLECT MONOLITHIC BASE DATA" step 312 to provide actual values for the AOI(s) of the patterned targets (e.g., patterned targets 491 in FIG. 4). As noted above, if a monolithic target is in relatively close proximity to a patterned target, measurements taken from the monolithic target will accurately represent the measurements of the patterned target. Note that according to another embodiment of the invention, if the expected value(s) for the measurement AOI(s) are well known (e.g., the process used to create the thin film is well characterized), step 312 can be skipped.

Next, "MODEL APPROXIMATION" step 320-1 (corresponding to step 320 in FIG. 3) begins with a "SPECIFY MODEL FORM" step 321, in which an expected mathematical form for the final empirical model is defined. This expected form can be based on any information related to the metrology operation being performed and the experimental data collected in step 310-1. For example, according to an embodiment of the invention, the expected mathematical form could be based on known theoretical models of similar systems.

According to another embodiment of the invention, the expected mathematical form of the model equations could be selected according to the shape of the experimental data. For example, a "smooth" form (e.g., polynomial) could be selected for the model equations if a graph of the experimental data gathered in step 311 exhibits smooth behavior (small number of peaks and valleys) relative to the independent measurement parameter (e.g., wavelength or angle of incidence). On the other hand, if the data exhibits non-smooth behavior (many peaks and valleys), a non-smooth form (e.g., oscillating function) could be selected. Note that according to another embodiment of the invention, a polynomial form could always be selected (at least initially), in an effort to maintain simplicity.

According to another embodiment of the invention, the expected mathematical form for the model equations could be generated by applying special correction factors to the standard (theoretical) mathematical form(s) for monolithic base layer structures. Those correction factors can include "grating factors" (i.e., factors that represent the effects of the grating layer(s)) and "space fill factors" (i.e., factors that represent the relative contributions from the grating elements and the filler material between grating lines). For example, a set of standard recursive equations (e.g., a set of lower reflectance equations generated using Equations 1-10) can be defined for the layers in the film stack, but with grating factors applied where a grating layer is present, the grating factors compensating for the optical effects of the grating layer.

According to an embodiment of the invention, the compensation provided by the grating factors can be enhanced by separating a grating layer into a "grating line" portion (i.e., the periodic lines that form the actual grating pattern) and a "space fill" portion (i.e., the filler material between the grating lines). A space fill factor can be applied to the model equations to adjust for the relative proportions of grating lines and space fill portions in the grating layer. Through the use of appropriate space fill and grating factors, the standard monolithic layer model equation (s) can be converted into an adjusted model equation (s) that is representative of the optical behavior of the grating layer.

For example, a grating factor g can be defined that represents the patterned layer (grating structure) optical effects, while a space fill factor f can be defined that represents and the relative contributions of the grating line and space fill portions (e.g., the fraction of the grating layer occupied by the space fill material). For ellipsometry measurements, an adjusted lower reflectance equation for a thin film layer "j" formed on a grating layer "j-1" might then be given by:

$$R_{BP}(j)=(1-f)*(g_p+(1+g_p)*R_{BGL}(j))+f*R_{BSF}(j) \quad [10a]$$

for p-polarized light (i.e., light polarized in the parallel (or transverse magnetic (TM)) direction), and:

$$R_{BS}(j)=(1-f)*(g_s+(1-g_s)*R_{BGL}(j))+f*R_{BSF}(j) \quad [10b]$$

for s-polarization (i.e., light polarized in the perpendicular (or transverse electric (TE)) direction), where $R_{BP}(j)$ is the lower reflectance of layer j for p-polarized light, $R_{BS}(j)$ is the lower reflectance of layer j for s-polarized light, $R_{BGL}(j)$ is the lower reflectance of layer j at a point above a grating line of grating layer j-1, and $R_{BSF}(j)$ is the lower reflectance of layer j at a point above a filler material portion of grating layer j-1, $g_p$ is the grating factor for p-polarized light, and $g_s$ is the grating factor for s-polarized light. Note that according to another embodiment of the invention, grating factors could be applied to the filler material terms $R_{BSF}(j)$ in Equations 10a and 10b.

Note that by setting space fill factor f and grating factors $g_p$ and $g_s$ equal to zero, adjusted equations 10a and 10b resolve to the standard monolithic base layer reflectance model equations (i.e., equations for a film stack formed on a monolithic base layer). Note further that grating factors $g_p$ and $g_s$ can themselves take almost any form, depending on the desired accuracy to be provided by the adjusted model equations. For example, according to an embodiment of the invention, the grating factors can be defined as constants. According to another embodiment of the invention, grating factors $g_p$ and $g_s$ can be defined as functions of the independent measurement parameter (e.g., wavelength or angle of incidence). For example, grating factor $g_p$ could be defined using a Cauchy form, as given below:

$$g_p=A_p+B_p/\lambda^2+C_p/\lambda^4 \quad [11]$$

where $A_p$, $B_p$, and $C_p$ are complex coefficients. According to another embodiment of the invention, the grating factors can even be functions of one or more of the attributes of interest (e.g., grating factors $g_p$ and $g_s$ can be functions of the thickness of the layer of interest).

Thus, equations 10a and 10b represent a monolithic layer formed on a grating layer, with grating factors being used to adjust the grating line-thin film interface reflectance to compensate for the non-monolithic nature of the grating layer. This adjusted reflectance (i.e., the term "$g_p+(1+g_p)$ *$R_{BGL}(j)$" in Equation 10a or the term "$g_s+(1-g_s)*R_{BGL}(j)$" in Equation 10b) is averaged with the space fill-thin film interface reflectance (i.e., the term "$R_{BSF}(j)$") according to space fill factor f (i.e., a weighted average is performed on the two terms with space fill factor f as the weighting factor). Note that if the film stack includes multiple grating layers, each of the different grating layer could have different (or the same) grating factors $g_p$ and $g_s$ and space fill factors f.

Lower reflectances $R_{BGL}(j)$ and $R_{BSF}(j)$ are simply represented using Equation 2, described above. For example, lower reflectance $R_{BGL}(j)$ can be given by the following:

$$R_{BGL}(j)=(R_{FGL}(j)+R_{TGL}(j-1))/(1+R_{FGL}(j)*R_{TGL}(j-1)) \quad [12]$$

where $R_{FGL}(j)$ is the interface Fresnel reflectance between layer j and a grating line in layer j-1, and $R_{TGL}(j-1)$ is the reflectance at the top of the grating line in layer j—1.

Then, using Equation 3, upper grating line reflectance $R_{TGL}(j-1)$ can be given by the following:

$$R_{TGL}(j-1)=R_{BGL}(j-1)\exp(-4\pi i^{nGL(j-1)d(j-1)\cos(\theta(j-1))/\lambda}) \quad [13]$$

where $R_{BGL}(j-1)$ is the lower grating line reflectance of layer j-1, $n_{GL}(j-1)$ is the index of refraction the grating line in layer j-1, d(j-1) is the thickness of layer j-1, and $\theta(j-1)$ is the angle of incidence of the probe beam as it enters layer j-1.

Using Equation 4, grating line index of refraction $n_{GL}(j-1)$ can be represented by the Cauchy equation:

$$n_{GL}(j-1)=A_{GL}(j-1)+B_{GL}(j-1)/\lambda^2+C_{GL}(j-1)/\lambda^4 \quad [14]$$

where $A_{GL}(j-1)$, $B_{GL}(j-1)$, and $C_{GL}(j-1)$ are Cauchy coefficients for index of refraction of the grating line material in layer j-1 and the wavelength λ of the probe beam. Note that various other equations can be used to define index of refraction. Note further that grating line index of refraction $n_{GL}(j-1)$ can also be replaced with a complex index of refraction $N_{GL}(j-1)$, as described above with respect to Equations 5 and 6.

Meanwhile, interface Fresnel reflectance $R_{FGL}(j)$ is given by the following:

$$R_{FGL}(j)=(p(j)-p_{GL}(j-1))/(p(j)+p_{GL}(j-1)) \quad [15]$$

where $p(j)$ and $p_{GL}(j-1)$ represent dispersion factors for layer j and a grating line of layer j−1, respectively. Dispersion factor $p(j)$ would be given by Equations 8 and 9 above, for light polarized in the parallel and perpendicular directions, respectively. Similarly, dispersion factor $p_{GL}(j-1)$ would be given by the following for light polarized in the parallel direction:

$$p_{GL}(j-1)=n_{GL}(j-1)\cos(\theta(j-1)) \quad [16]$$

and by the following for light polarized in the in the perpendicular direction:

$$p_{GL}(j-1)=\cos(\theta(j-1))/n_{GL}(j-1) \quad [17]$$

In a manner similar to that described with respect to Equations 13 through 17, lower space fill reflectance RBSF(j) can be defined, with the appropriate space fill parameters replacing the grating line parameters used in the determination of lower grating line reflectance RBGL(j). Thus, the expected mathematical form includes a set of recursive equations (or two sets of recursive equations, for light polarized in the parallel and perpendicular directions) with Equation 11 providing the model equation for a layer(s) in the film stack formed on a grating layer, and Equation 2 providing the model equations for the layers in the film stack that are not formed on a grating layer.

Note that according to another embodiment of the invention, the reflectance terms in Equations 10a and 10b could be replaced with transmittance terms for reflectometry measurements. For example, the lower reflectance term $R_{BGL}(j)$ for the thin film-grating line interface in Equations 10a and 10b could be replaced with lower transmittance term $F_{BGL}(j)$ for the thin film-grating line interface, indicated by the following:

$$F_{BLG}(j) = \left(\frac{p(j)+p_{GL}(j-1)}{2P(j)}\right)(1+R_{FGL}(j)*R_{TGL}(j-1))*F_{TGL}(j-1) \quad [18]$$

where $p(j)$ and $p_{GL}(j-1)$ represent dispersion factors for layer j and a grating line of layer j−1, respectively, $R_{FGL}(j)$ is the interface Fresnel reflectance between layer j and a grating line in layer j−1, and $R_{TGL}(j-1)$ is the reflectance at the top of the grating line in layer j−1, and $F_{TGL}(j-1)$ is the transmittance at the top of the grating line in layer j−1, just as described above with respect to Equation 12.

Upper grating line transmittance $F_{TGL}(j-1)$ can then be defined as:

$$F_{TGL}(j-1)=F_{BGL}(j-1)/\exp(-2\pi i^{nGL(j-1)d(j-1)\cos(\theta(j-1))/\lambda}) \quad [19]$$

where $R_{BGL}(j-1)$ is the lower grating line reflectance of layer j−1, $n_{GL}(j-1)$ is the index of refraction the grating line in layer j−1, $d(j-1)$ is the thickness of layer j−1, and $\theta(j-1)$ is the angle of incidence of the probe beam as it enters layer j−1, just as described above with respect to Equation 13.

The lower reflectance term $R_{BSF}(j)$ for the thin film-space fill interface in Equation 12 could be replaced with lower transmittance term $F_{BSF}(j)$ for the thin film-space fill interface. The space fill lower transmittance term $F_{BSF}(j)$ would be defined in much the same manner as described above for grating line lower transmittance term $F_{BGL}(j)$. Note that when solving the recursive transmittance equations, the transmittance at the substrate is defined to be zero (in contrast to the substrate reflectance, which is equal to one, as noted above).

In any case, once the expected mathematical form for the empirical model is defined, the coefficients of that expected mathematical form are adjusted according to the experimental data in a "REGRESS ALONG COEFFICIENTS" step 322. Specifically, variables in the model equations making up the expected mathematical form are set to an expected or measured (step 312) value(s). Then, the model equations are regressed along their coefficients (e.g., grating factors $g_p$ and $g_s$ in Equations 10a and 10b, respectively). When the output of the model equations matches the experimental data gathered in step 311, the model equation coefficients are fixed in a "FINALIZE MODEL EQUATIONS" step 323 to complete the empirical model.

As noted above, because the empirical model is generated by simple regression, rather than by actually solving a set of equations, the empirical model can be created much more rapidly than can a conventional theoretical model. Note also that because conventional optical metrology tools already include regression capabilities (for determining AOI output values from the theoretical model), conventional tools can be readily adapted to perform steps 321-323 to generate the empirical model.

Once the empirical model has been finalized, measurements can be taken from patterned target locations on calibration additional test samples, and the empirical model can be used to determine values for the attributes of interest in a "COLLECT MEASUREMENT DATA" step 330, a "REGRESS ALONG ATTRIBUTE(S)" step 340, and an "OUTPUT ATTRIBUTE VALUE(S)" step 350 (described in detail with respect to FIG. 3). Note that steps 330, 340, and 350 are substantially similar to what would be performed in a conventional metrology operation. The only difference is that the model regression in step 340 is performed on an empirical model, while a conventional metrology operation would perform the regression on a theoretical model. Therefore, the invention can be easily incorporated into existing metrology systems.

Figure 6A:
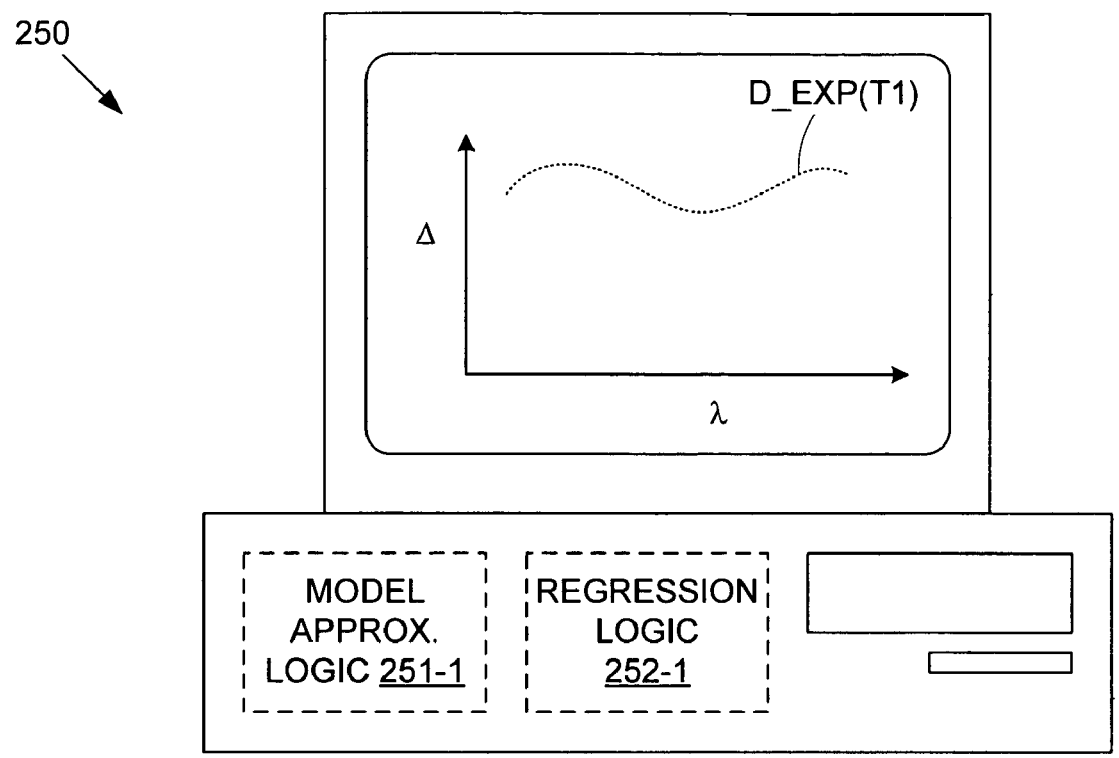
FIGS. 6A-6F are stages in a method for determining thin film attribute values using an empirical model, according to an embodiment of the invention.

FIGS. 6A-6E provide an exemplary depiction of the process described with respect to FIG. 5. In FIG. 6A, data processing resources 250-1 gathers experimental data D_EXP at a known value T1 of a thin film attribute of interest T (corresponding to step 311 in FIG. 5). Note that while a graph of delta (Δ) versus wavelength (λ) is depicted for exemplary purposes, delta and wavelength could be replaced with any other optical metrology measurement parameters (e.g., reflectance and angle of incidence).

Meanwhile, an expected mathematical form MF_EXP is defined in model approximation logic 251-1 (step 321). For exemplary purposes, expected mathematical form MF_EXP is a function of attribute variable T, and includes coefficients A, B, and C. According to an embodiment of the invention, expected mathematical form MF_EXP can be entered by a user via an interface to data processing resources 250-1 (e.g., a graphical user interface or a command line interface). According to another embodiment of the invention, a user could select expected mathematical form MF_EXP from a group of mathematical forms stored in data processing resources 250-1 or stored at a remote location.

Figure 6B:
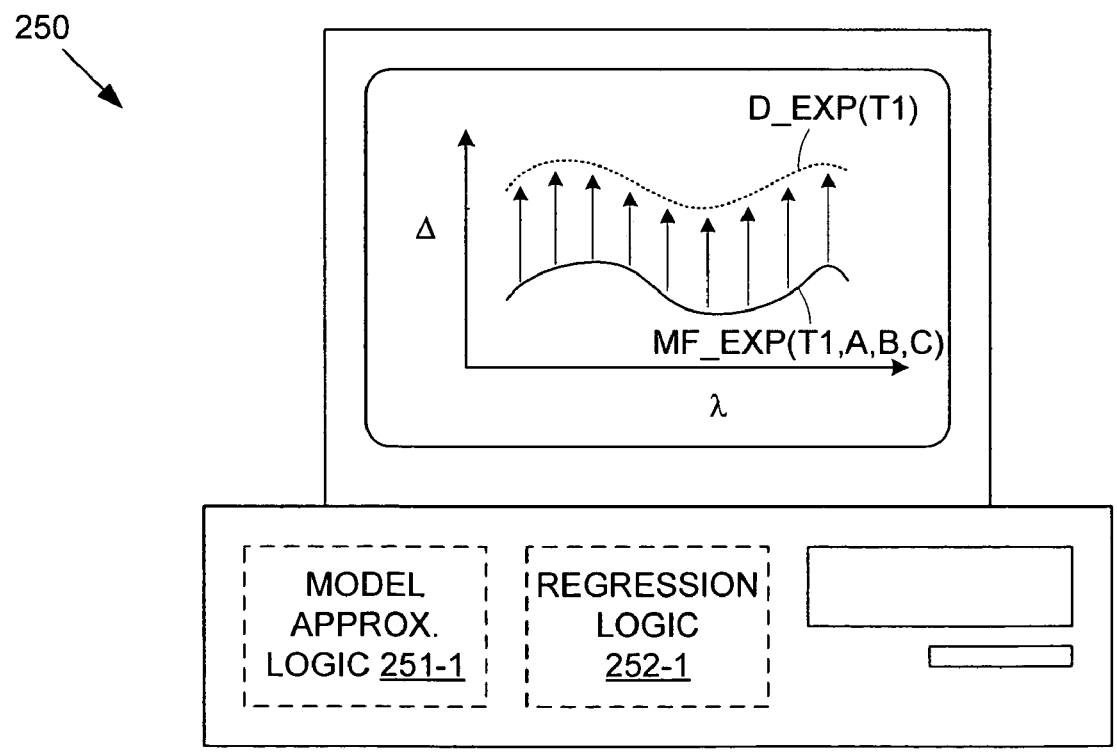
Figure 6C:
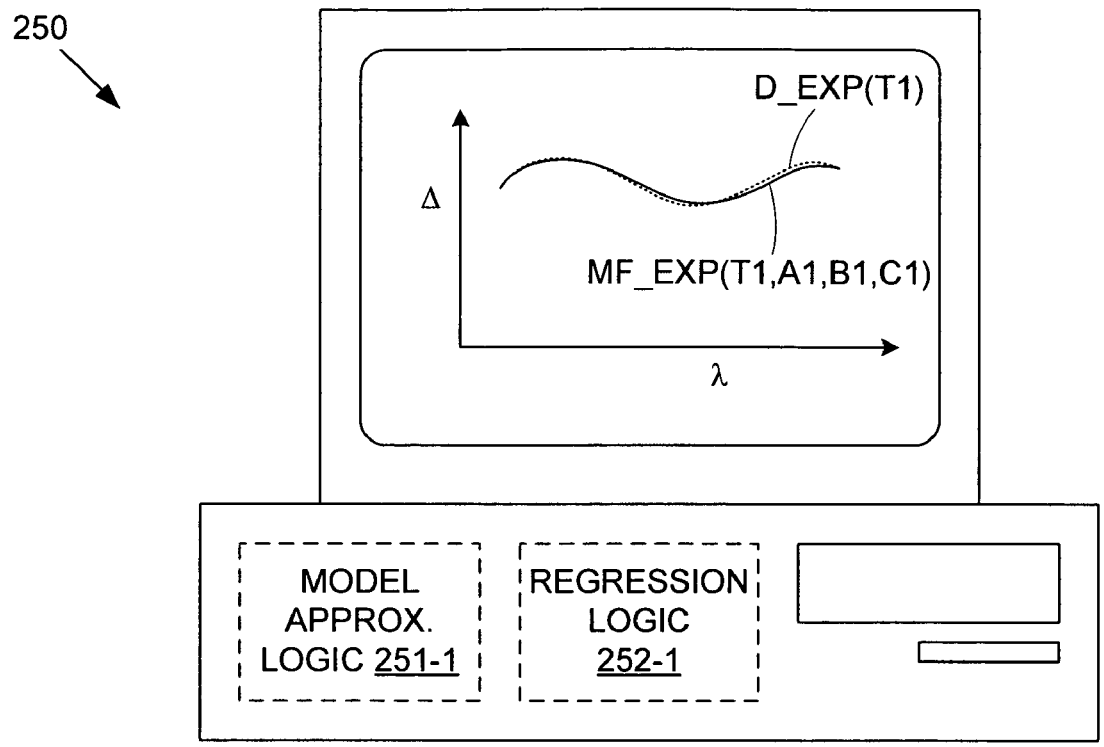

In FIG. 6B, known value T1 (either an expected value or a measured value from step 312) is substituted into the empirical model form MF_EXP(T,A,B,C). Empirical model form M_EXP(T1,A,B,C) is then regressed along coefficients A, B, and C (step 322) by regression logic 252-1. When empirical model form MF_EXP(T1,A1,B1,C1) matches experimental data D_EXP(T1) (i.e., is within a predetermined tolerance band of experimental data D_EXP(T1)), as shown in FIG. 6C, coefficients A, B, and C are fixed at values A1, B1, and C1 (step 323) to finalize an empirical model M_EMP(T,A1,B1,C1). Note that if multiple sets of experimental data are present, simultaneous regression can be performed for each of the sets of experiments data, and the values of coefficients A, B, and C can be set when each of the regression outputs is within a predetermined tolerance band TOL of its associated experimental data.

Figure 6D:
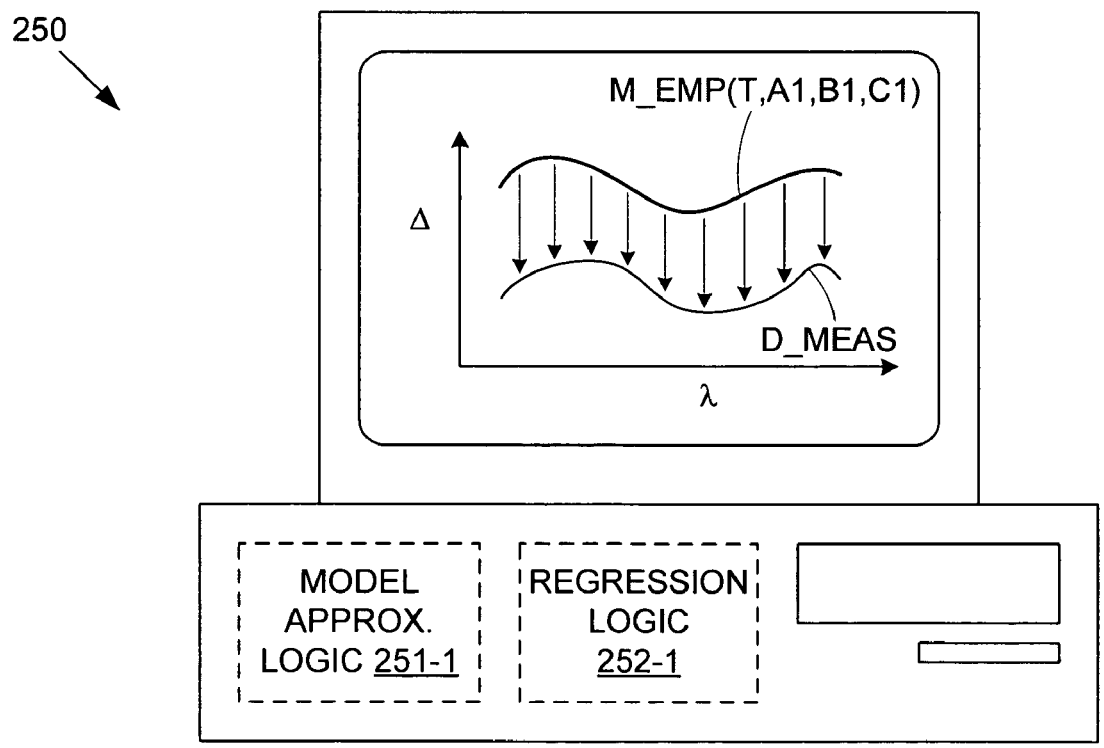
Figure 6E:
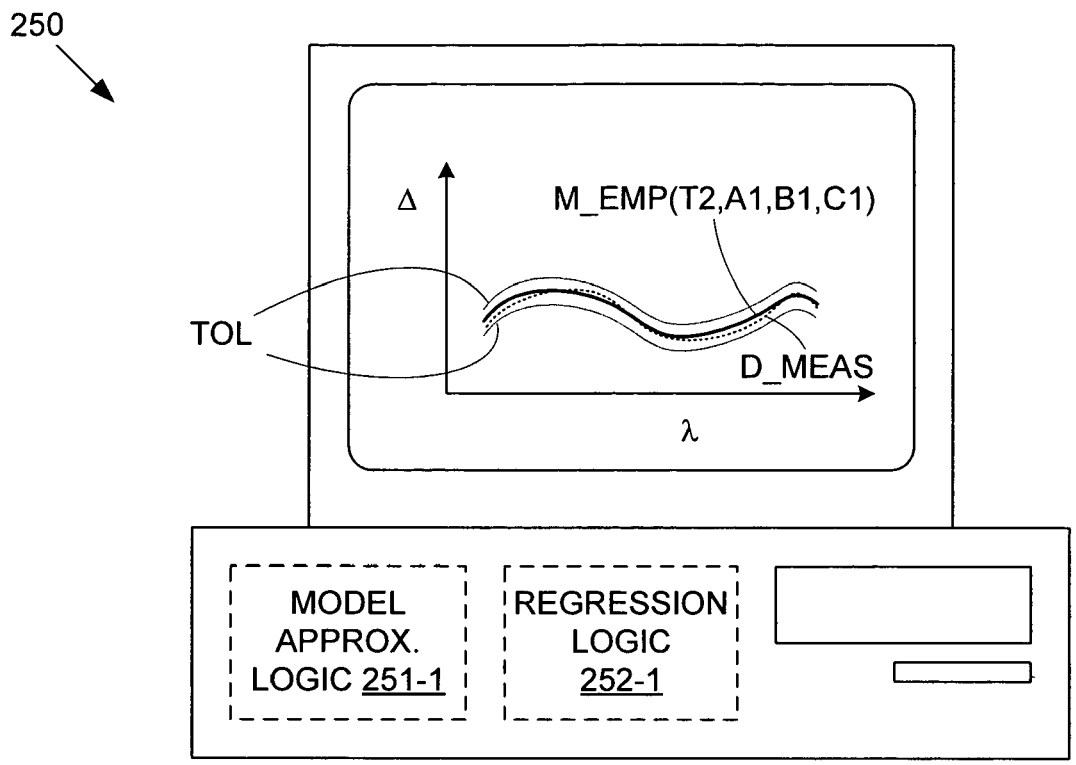

When a new set of measurement data D_MEAS is taken from a new test sample (step 330), empirical model M_EMP (T,A1,B1,C1) is regressed along attribute T by regression logic 252-1, as shown in FIG. 6D (step 340). The value T2 of attribute T that causes empirical model M_EMP(T,A1, B1,C1) to match measurement data D_MEAS (i.e., generate an empirical model output that is within a predetermined tolerance band of measurement data D_MEAS), as shown in FIG. 6E, can then be provided by data processing resources 250-1 as the output value of attribute T (step 350). In this manner, the empirical model generated in FIG. 6C via regression can be used to perform optical metrology on any number of additional test samples.

Note that when a new set of measurement data D_MEAS is taken from a new test sample (step 330), and an empirical model M_EMP(T,A1,B1,C1) is regressed along AOI T by regression logic 252-1, as shown in FIG. 6D (step 340), the values of coefficients A, B, and C may be initially treated as constant and fixed at their respective predetermined values of A1, B1, and C1, respectively. Alternatively, coefficients A, B, and C could always be set to a predetermined nominal values that would result in zero correction to the nominal reflectance as computed for a film stack with grating factors $g_p$ and $g_s$ equal to zero.

Also, additional refinement of the regression process can be achieved by allowing the regression logic to regress with AOI T held at its predetermined value of T2. In doing so, the quality of fit can be improved.

Figure 6F:
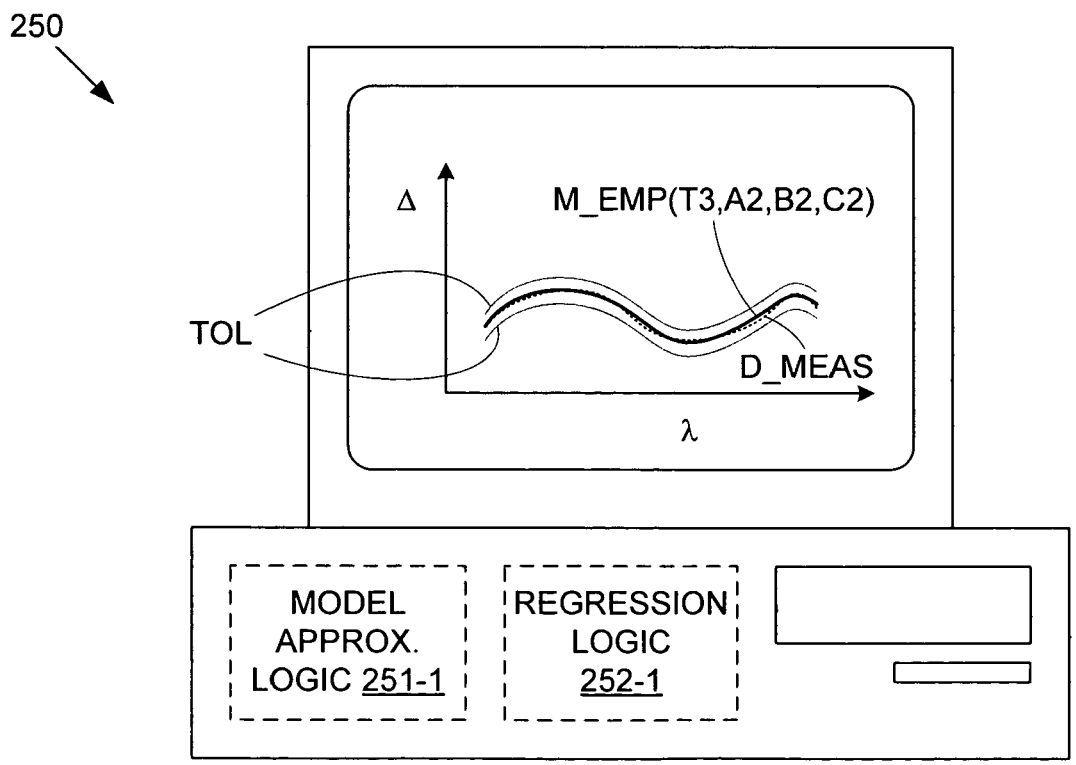

Alternatively (or subsequently), simultaneous regression of AOI T (from the predetermined value of T2) with coefficients A, B, and C can be performed to generate a new empirical model M_EMP(T3, A2, B2, C2), as shown in FIG. 6F. This can result in a new value T3 for AOI T that improves the match with measurement data D_MEAS, thereby providing improved measurement quality.

Figure 7:
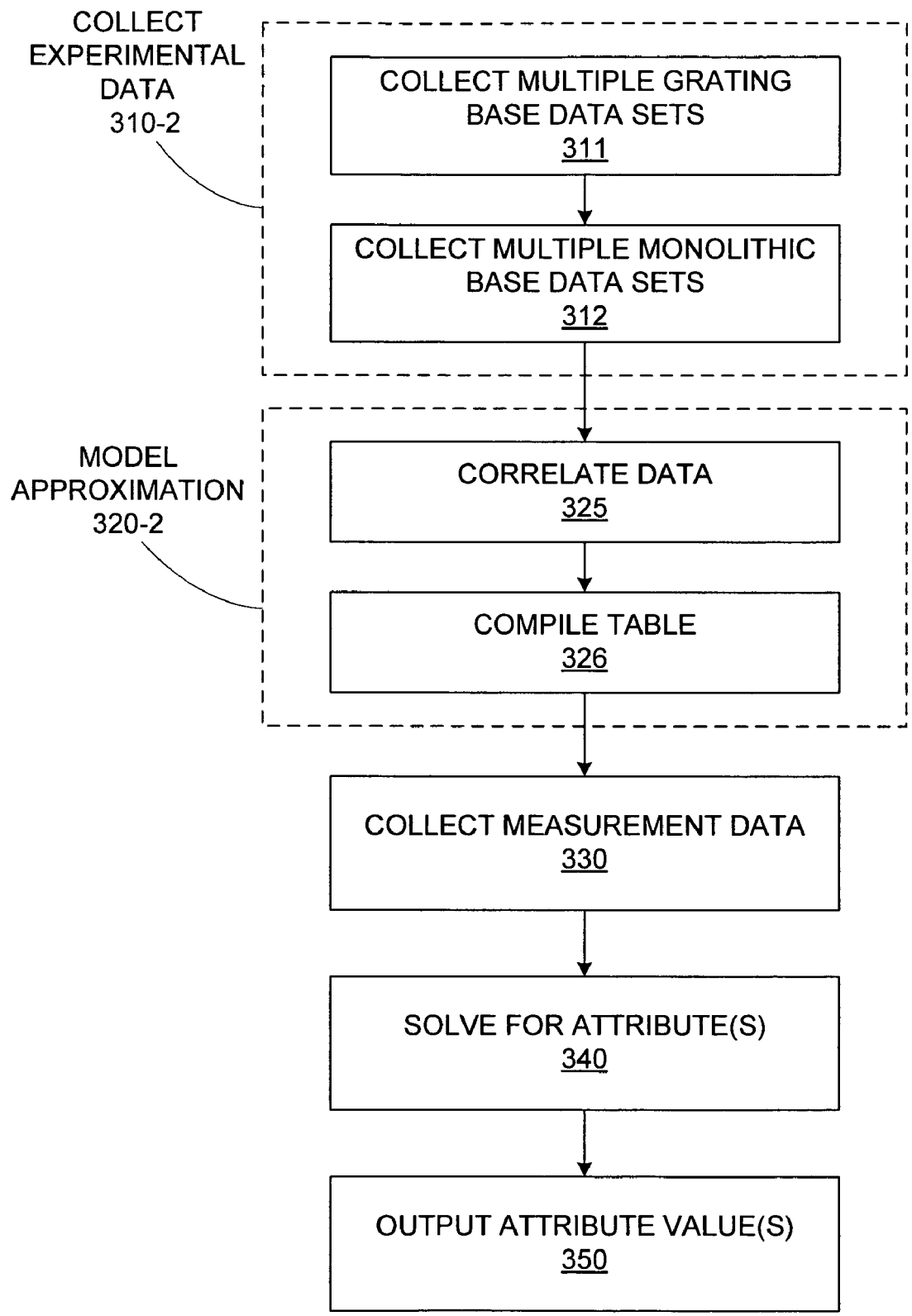
FIG. 7 is a flow diagram of a method for determining thin film attribute values using a lookup model, according to an embodiment of the invention.

As noted above, according to another embodiment of the invention, an empirical model can be created as a lookup model by compiling multiple sets of experimental data. FIG. 7 shows a detailed embodiment of the flow chart of FIG. 3, including sub-steps specific to the use of an empirical lookup model, according to an embodiment of the invention. A "COLLECT EXPERIMENTAL DATA" step 310-2 (corresponding to step 310 in FIG. 3) begins with a "COLLECT MULTIPLE PATTERNED BASE DATA SETS" step 311 in which experimental data sets are gathered from multiple patterned targets. The multiple patterned targets include at least two patterned targets for which the values for an AOI(s) are different. According to an embodiment of the invention, the multiple patterned targets can be included in a single test sample, with differing process parameters at each patterned target providing the desired attribute value variations. According to another embodiment of the invention, patterned target measurements can be taken from multiple test samples to provide the desired number of different values for the AOI(s).

Actual values for those various attributes of interest can be determined in an optional "COLLECT MULTIPLE MONOLITHIC BASE DATA SETS" step 312, in which measurements of those attributes of interest are taken from monolithic targets (e.g., monolithic targets 492 in FIG. 4) in close proximity to the patterned targets (e.g., patterned targets 491 in FIG. 4). The thin film attribute values determined from measurements at the monolithic targets can then be used as the attribute values for the patterned targets. Note that according to another embodiment of the invention, if the expected values of the thin film attributes for the various patterned targets are well known (e.g., the processes used to create the thin films are well characterized), step 312 can be skipped.

Next, "MODEL APPROXIMATION" step 320-2 (corresponding to step 320 in FIG. 3) begins with a "CORRELATE DATA" step 325, in which the experimental data set from each patterned target is correlated with the AOI value(s) for that patterned target. The experimental data sets are then compiled into a database with the AOI(s) as the lookup parameter(s) in a "COMPILE TABLE" step 326, thereby creating the empirical lookup model. Increasing the number of data sets associated with different attribute values collected in step 311 can increase the resolution (if the different attribute values are closely spaced) or the range (if the different attribute values are widely spaced) of the lookup model.

Because the empirical lookup model is simply a collection of data, minimal computing resources are required for its creation. Therefore, just as with the empirical mathematical model described above with respect to FIGS. 5 and 6A-6E, the empirical lookup model can be generated much more quickly and easily than the conventional theoretical model for patterned targets. Note that according to another embodiment of the invention, an empirical lookup model can be generated by substituting multiple different AOI values into an empirical mathematical model developed in the manner described above.

Once the empirical lookup model has been finalized, measurement data is gathered from one or more patterned-based targets on a test sample having an unknown value(s) for the AOI(s) in a "COLLECT MEASUREMENT DATA" step 330. The measured data is compared with the lookup model, which interpolates the data in the empirical lookup model for each wavelength and angle of incidence along the AOI(s) in a "SOLVE FOR ATTRIBUTE(S)" step 340, and the calculated attribute value is output in an "OUTPUT ATTRIBUTE VALUE(S)" step 350.

Note that the interpolation of step 340 can apply any desired interpolation algorithm, such as cubic spline interpolation or quadratic interpolation. The actual interpolation can be performed using the existing regression capabilities of an optical metrology tool, thereby simplifying the implementation of the invention.

Figure 8A:
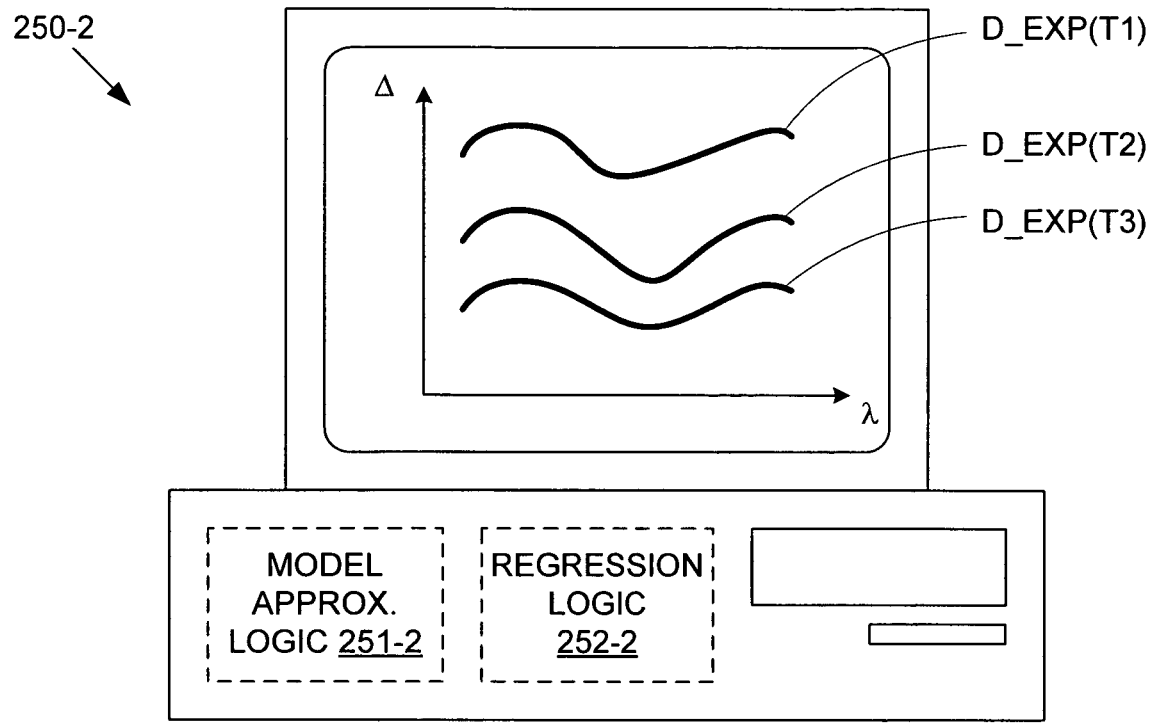
FIGS. 8A-8D depict a method for determining thin film attribute values using a lookup model, according to an embodiment of the invention.

FIGS. 8A-8D provide an exemplary depiction of the process described with respect to FIG. 7, according to an embodiment of the invention. In FIG. 8A (corresponding to step 310-2 of FIG. 7), data processing resources 250-2 gathers multiple experimental data sets D_EXP from patterned targets having different values of an AOI T (i.e., T1, T2, and T3). Note that while a graph of delta (Δ) versus wavelength (λ) is depicted for exemplary purposes, delta and wavelength could be replaced with any other optical metrology measurement parameters (e.g., reflectance and angle of incidence).

Figure 8B:
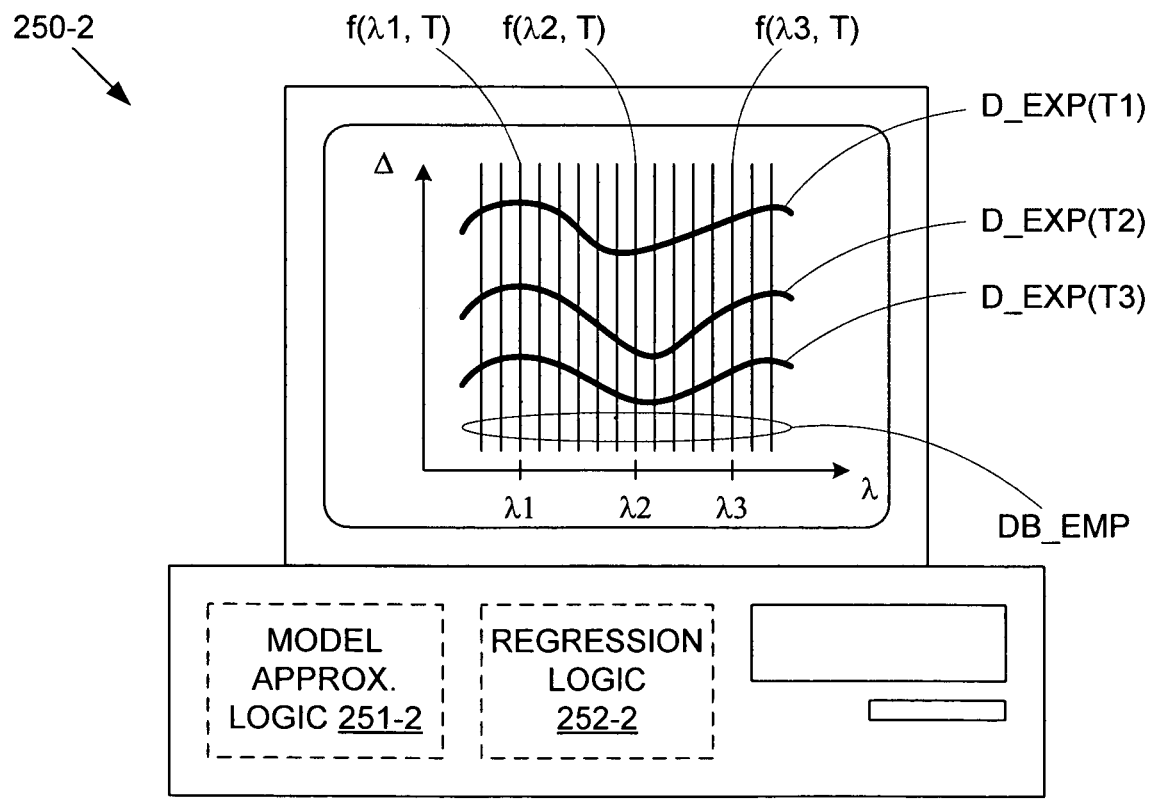
Figure 8C:
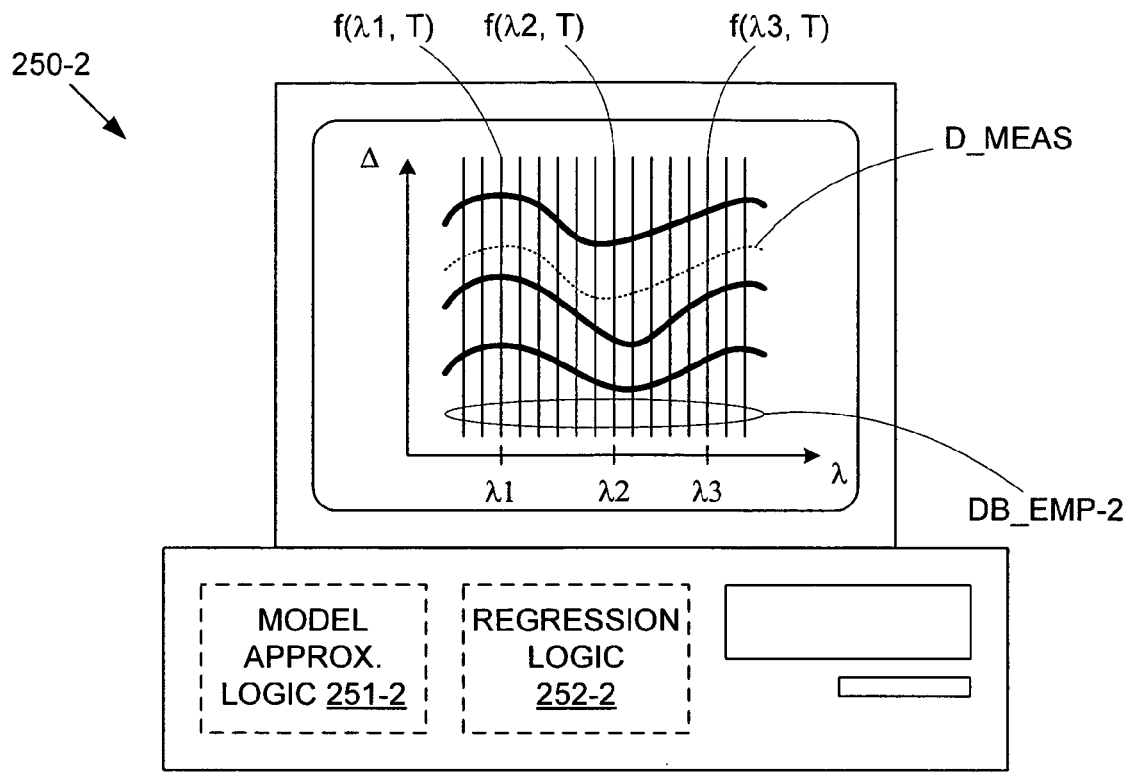

Experimental data sets D_EXP(T1), D_EXP(T2), and D_EXP(T3) are then compiled into an empirical lookup model DB_EMP-2 by model approximation logic 251-2 in FIG. 8B (step 320-2). Then, in FIG. 8C, a new set of measurement data D_MEAS is taken from a new test sample (step 330), and the data in the lookup model is interpolated by regression logic 252-2 to determine a value for the AOI(s). Various methods of interpolation will be readily apparent.

Figure 8D:
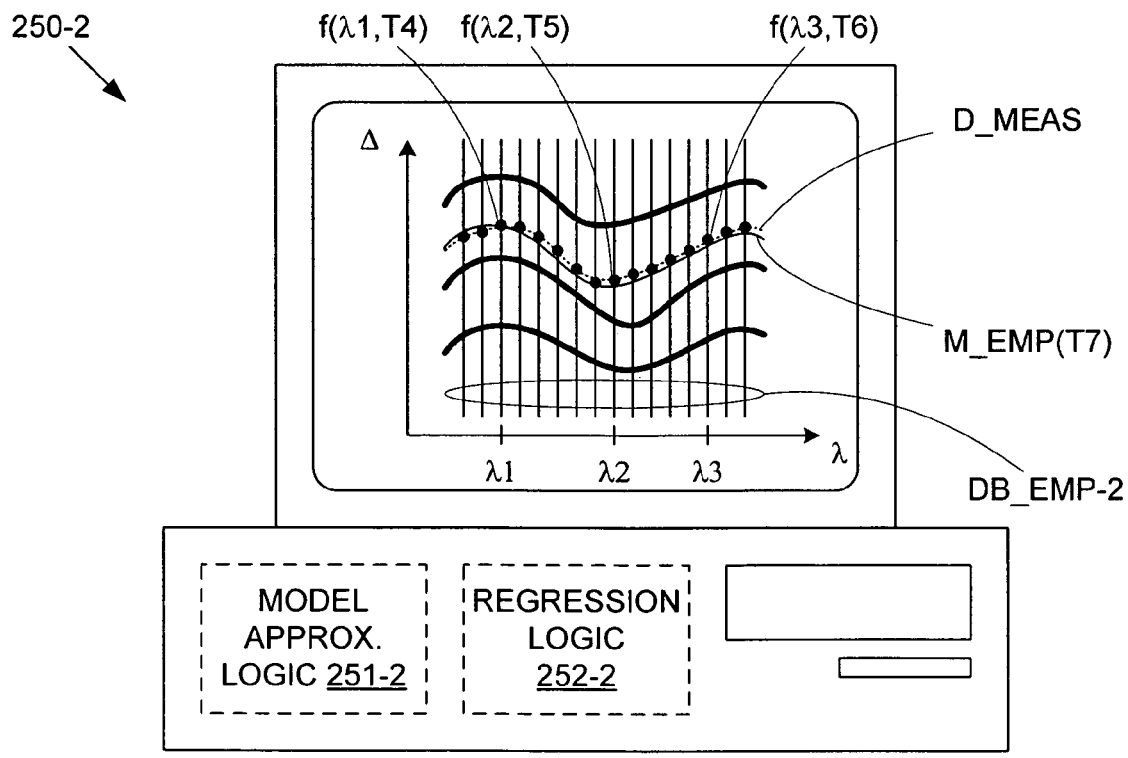

For example, the experimental data sets in a lookup model (e.g., D_EXP(T1), D_EXP(T2), and D_EXP(T3)) can be used to define a measurement function at each wavelength. In other words, for a given wavelength (or angle of incidence), the measurement value (A in this case) can be represented as a function of the AOI. For instance, at wavelengths λ1, λ2, and λ3, the value of Δ can be represented by functions f(λ1,T), f(λ2,T), and f(λ3,T), respectively. Then, by interpolating along the AOI in those functions as shown in FIG. 8D, a set of interpolated values for AOI T can be determined at each wavelength (e.g., values T4, T5, and T6 at wavelengths λ1, λ2, and λ3). A final output value for AOI T can then be determined from this set of interpolated values T4, T5, and T6 by various methods, including averaging the values, selecting the median value, or performing a weighted average, among others.

Alternatively, simultaneous global interpolation may be employed for a set of functions (e.g., f(λ1,T), f(λ2,T), and f(λ3,T)) via regression on the AOI (T in this case). By generating an empirical model output (e.g., curve M_EMP (T7)) that is within a predetermined tolerance band of measurement data D_MEAS, a final output value for AOI T (e.g., T7) can be determined.

Figure 9A:
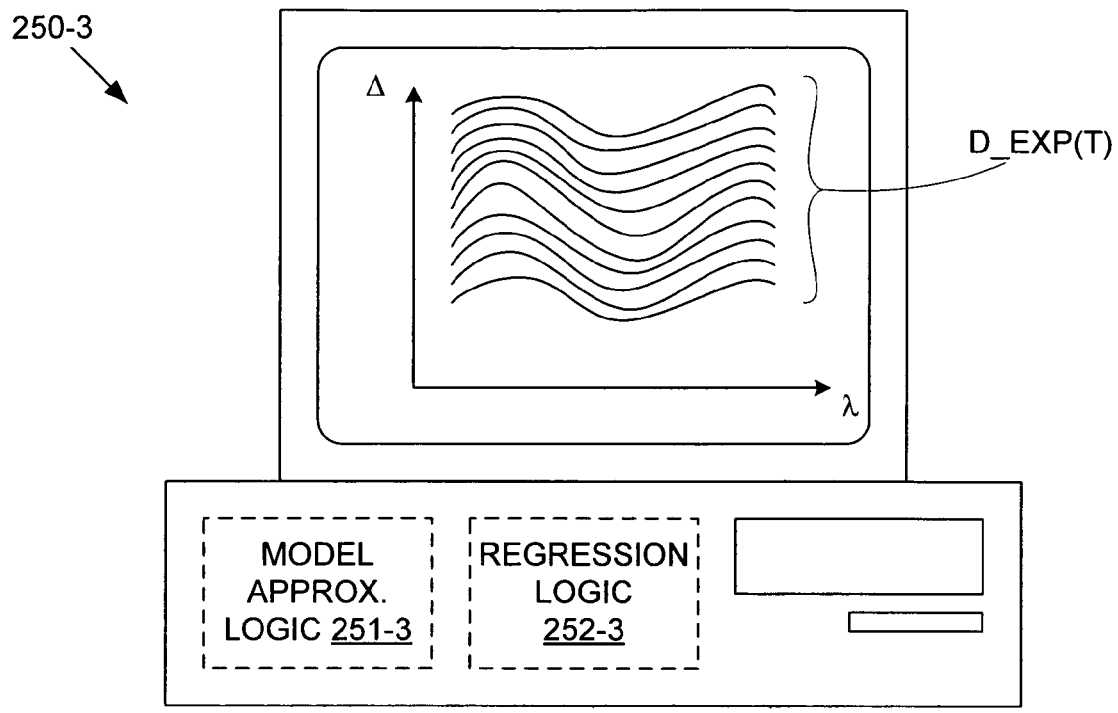
FIGS. 9A-9D depict a method for determining thin film attribute values using a lookup model, according to another embodiment of the invention.

FIGS. 9A-9D provide an exemplary depiction of the process described with respect to FIG. 7, according to another embodiment of the invention. In FIG. 9A (corresponding to step 310-2 of FIG. 7), data processing resources 250-3 gathers multiple experimental data sets D_EXP(T) from patterned targets having different values of an AOI T (i.e., T1, T2, and T3). Note once again that while a graph of delta (Δ) versus wavelength (λ) is depicted for exemplary purposes, delta and wavelength could be replaced with any other optical metrology measurement parameters (e.g., reflectance and angle of incidence).

Figure 9B:
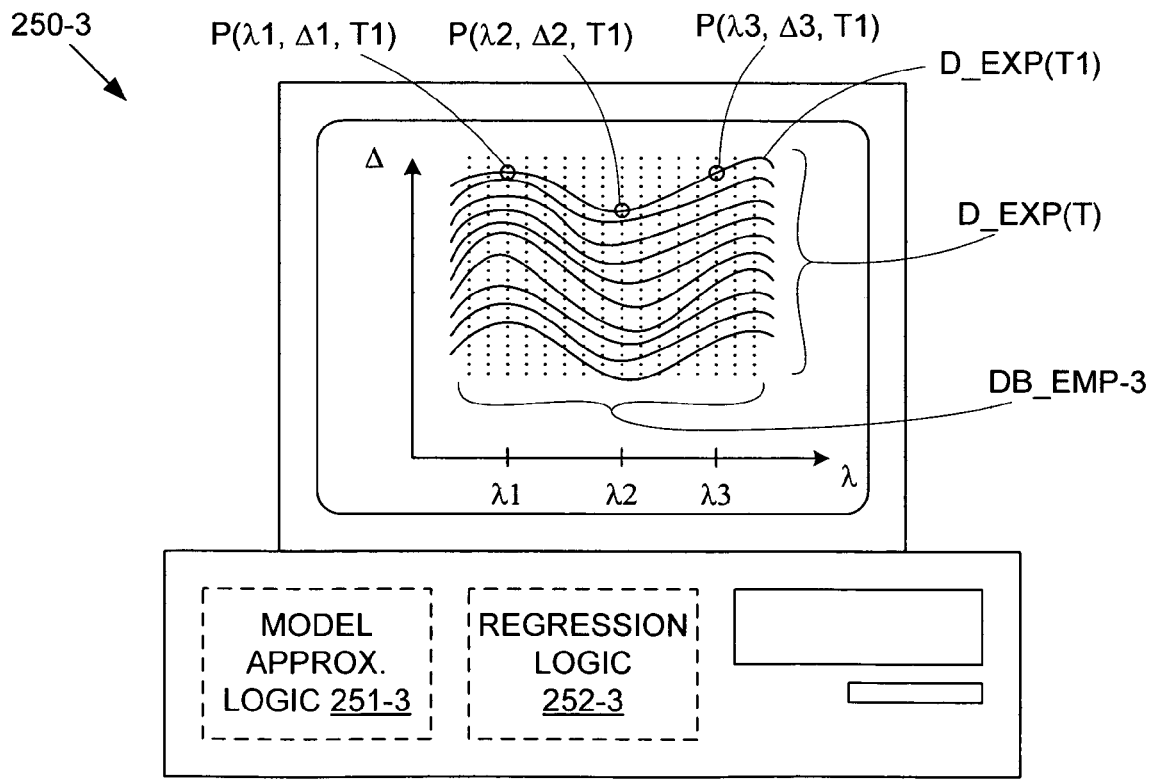

Experimental data sets D_EXP(T) are then compiled into an empirical lookup model DB_EMP-3 by model approximation logic 251-3 in FIG. 9B (step 320-2). Empirical lookup model DB_EMP-3 is simply a collection of reference data points, each of which represents the AOI value for a particular set of measurement parameters (in this case, for a particular wavelength/delta combination). For example, all the reference data points derived from an experimental data set D_EXP(T1) will represent wavelength/delta combinations corresponding to an AOI value of T1—e.g., reference data points P(λ1, Δ1, T1), P(λ2, Δ2, T1), and P(λ3, Δ3, T1). Note that empirical lookup model DB_EMP-3 is a data point-based model, unlike empirical lookup model DB_EMP-2 described with respect to FIG. 8B, which is made up of a set of functions.

Figure 9C:
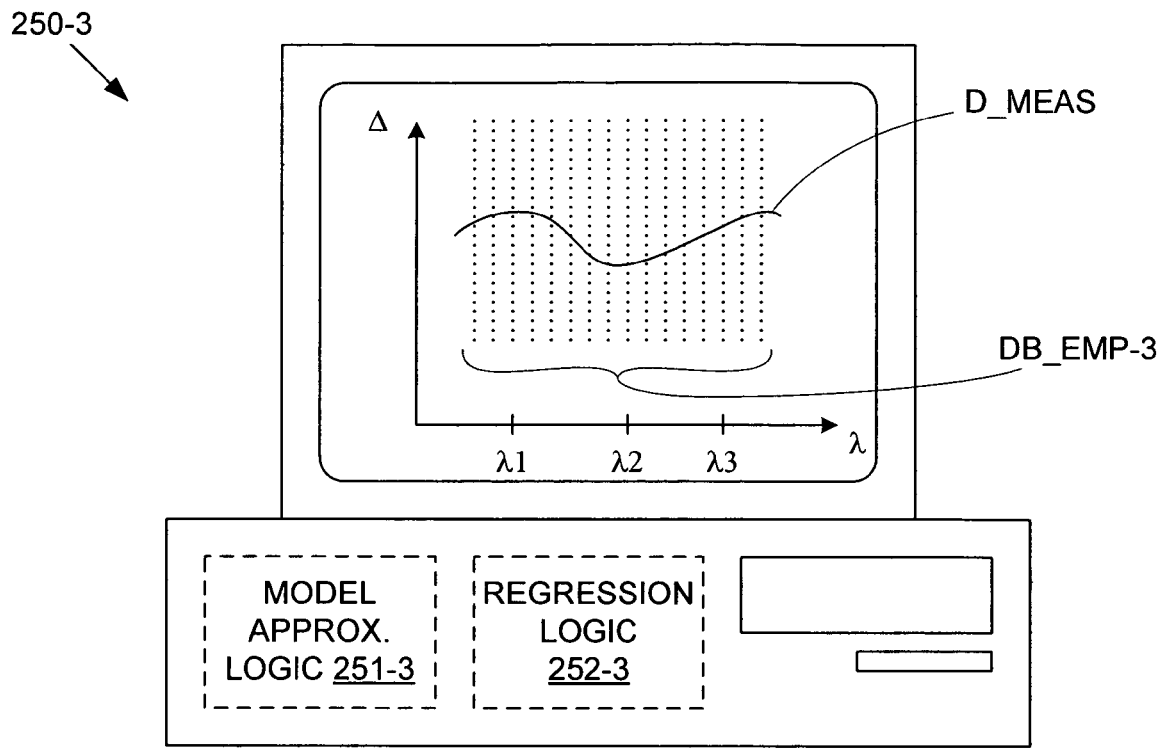
Figure 9D:
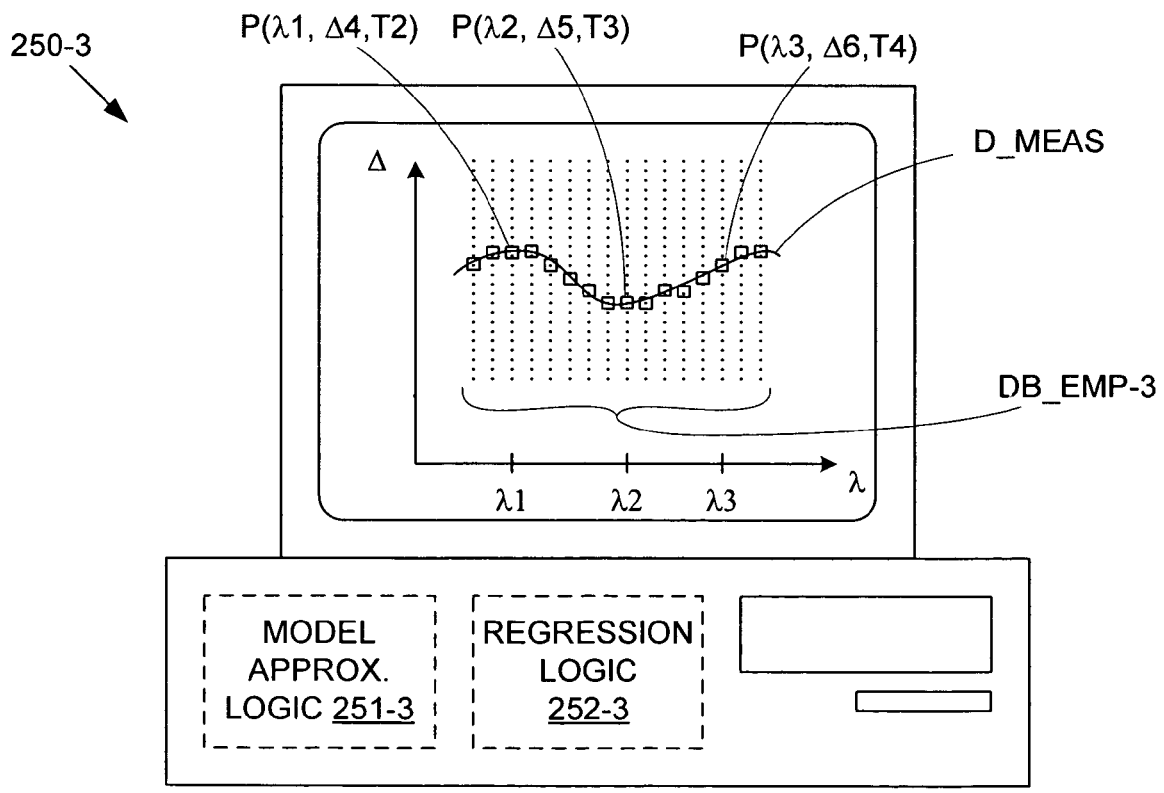

In FIG. 9C, a new set of measurement data D_MEAS is taken from a new test sample (step 330) and is compared to the reference data points of empirical lookup model DB_EMP-3. The reference data points that match measurement data D_MEAS (e.g., are within a predetermined tolerance band of measurement data D_MEAS) are determined in FIG. 9D, as indicated by the circled reference data points (e.g., reference data points P(λ1, Δ4, T2), P(λ2, Δ5, T3), and P(λ3, Δ6, T4). The reference data points derived from this fitting operation can then be used to generate an output value for the AOI (step 340) by various methods (e.g., taking the mean or median of the AOI values of the matching data points). In this manner, empirical lookup model DB_EMP provides a simple means for providing optical metrology for patterned-based thin film layers.

Note that according to another embodiment of the invention, the lookup model can be based on grating factors (correction factors that compensate for grating base layer-induced deviations from the monolithic base layer results), rather than measured data. In other words, instead of creating the lookup model by simply compiling the raw experimental data measured from each patterned target, the lookup model could be created by converting that raw experimental data into grating factors associated with the patterned targets.

Figure 10:
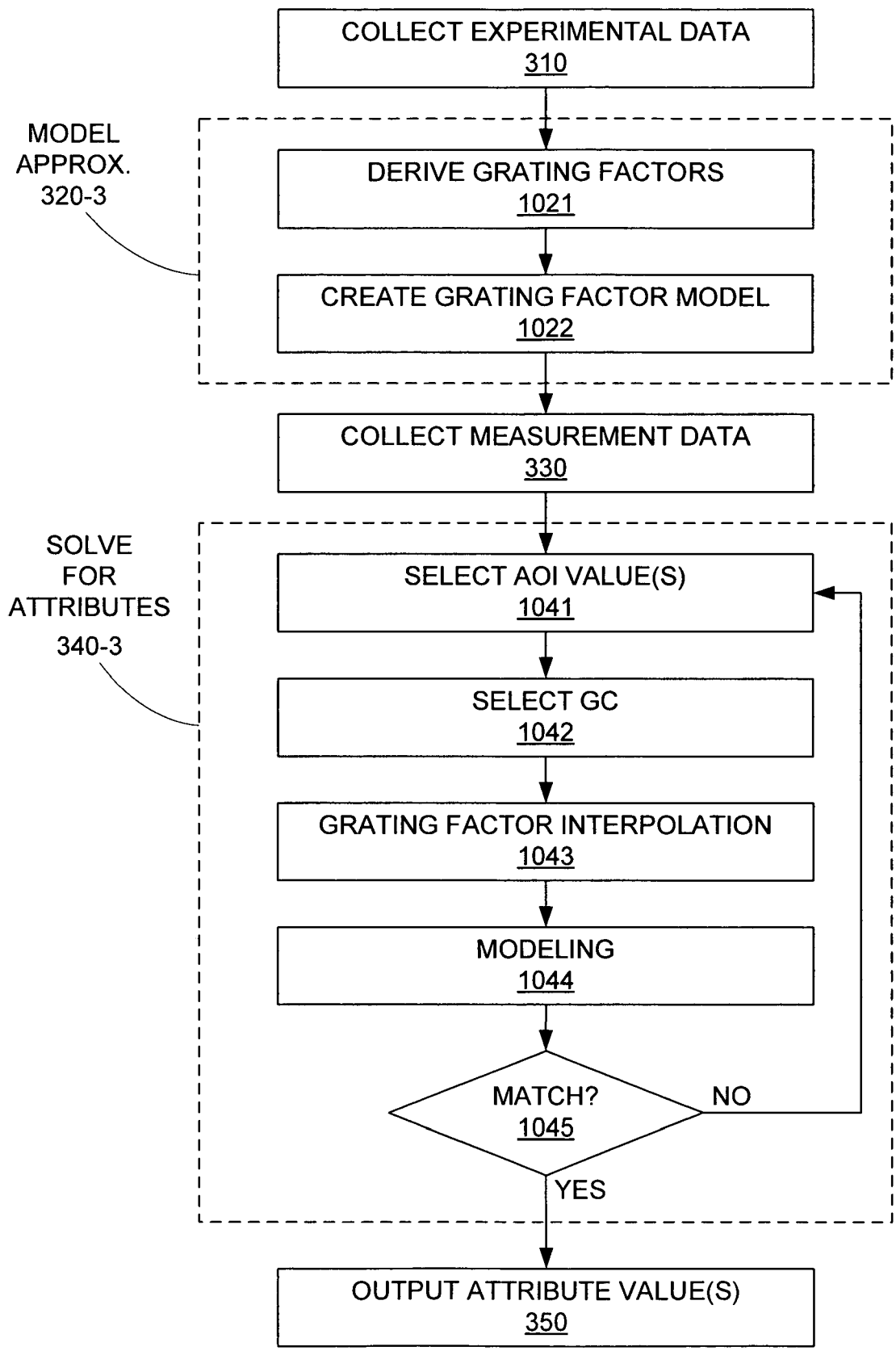
FIG. 10 is a flow diagram of a method for determining thin film attribute values using an empirical model, according to another embodiment of the invention.

FIG. 10 shows a detailed embodiment of the flow chart of FIG. 3, including sub-steps specific to the use of a grating factor lookup model, according to an embodiment of the invention. During a "COLLECT EXPERIMENTAL DATA" step 310 (which is substantially similar to steps 311 and 312 described with respect to FIGS. 5 and 7), experimental data sets are gathered from multiple patterned targets.

According to an embodiment of the invention, the multiple patterned targets can include thin film layers having different attribute of interest values, formed on patterned base layers having substantially the same geometries. According to another embodiment of the invention, the multiple patterned targets can include thin film layers having different attribute of interest values formed on patterned base layers having different geometries. According to various other embodiments of the invention the experimental data can be gathered from a single tool or multiple tools.

Note that according to an embodiment of the invention, the effects of noise (i.e., measurement variability) in a particular tool can be compensated for by taking repeat measurements using the same calibration test sample(s). The experimental data gathered from the multiple measurements can then either be averaged or used as independent experimental data sets, thereby reducing the effects of random measurement variations generated within the particular metrology tool.

Note further that according to another embodiment of the invention, the effects of systemic measurement variability among a group of metrology tools can be reduced by taking measurements from the same calibration test sample(s) from all of the metrology tools in the group. Then, by incorporating the experimental data from each of the metrology tools into the subsequently derived empirical model, the empirical model is effectively matched to all the tools, rather than being overly biased towards any one tool (i.e., the same empirical model can be used with any of the metrology tools, thereby eliminating the need to generate a different model for each tool).

Note that either of the aforementioned techniques (i.e., multiple measurements of the same calibration test sample(s) using a single toll, and measurements of the same calibration test sample(s) using multiple tools) can also be applied during the experimental data collection steps described with respect to FIGS. 3, 5, and 7. Furthermore, the techniques can be applied to any metrology tool or group of metrology tools in which modeling based on experimental data is used.

Next, "MODEL APPROXIMATION" step 320-3 (corresponding to step 320 in FIG. 3) begins with a "DERIVE GRATING FACTORS" step 1021, in which the adjusted model equations for the patterned targets (e.g., adjusted model equations 10a and 10b) are solved using the experimental data sets to generate a set of values for the grating factors (e.g., grating factors $g_p$ and $g_s$). As described above, the grating factors are correction factors that adjust the standard (monolithic base layer) equations to compensate for the optical effects introduced by the patterned base layer(s). The grating factors can take any form (e.g., constant, polynomial, sine wave or oscillator function), depending on desired accuracy of the compensation provided by those grating factors. Note further that the grating factor values can comprise discrete values or continuous functions.

The grating factor values are then compiled into a lookup model in a "CREATE GRATING FACTOR MODEL" step 1022. Note that the particular structure of this grating factor lookup model depends on the form of the grating factors themselves.

For example, according to an embodiment of the invention, each grating factor can comprise a function of the independent measurement parameter (e.g., wavelength or angle of incidence) that is specific to a particular combination of patterned base layer geometry (e.g., grating line size, proportion of grating line to filler material) and attribute of interest value(s). As described in greater detail below with respect to FIG. 11B and 11C, the grating factor model can then comprise a multidimensional table, wherein the specific table dimension depends on the number of different AOIs and patterned base layer geometries.

Note that each different patterned base layer geometry will be associated with its own set of grating factor values. For example, if the experimental data is taken from patterned targets having two different patterned base layer geometries, then certain grating factor values derived from that experimental data will be associated with one base layer geometry and other grating factor values will be associated with the other base layer geometry.

Note further that because the effects of any particular patterned base layer geometry can be contained within the grating factor values associated with that patterned base layer geometry, the actual base layer geometry details need not be known. Because the different patterned base layer geometries are simply used as identifiers (labels) to segregate the various grating factor values, the geometry details are not critical.

For example, if experimental data (and later, measurement data) is taken from patterned targets having one of three different patterned base layer geometries, all that need be known is which of those three geometries a particular set of data is associated with. The data can then be classified and processed appropriately, without ever knowing the details of its associated patterned base layer geometry. If the adjusted model equations include a space fill factor to account for grating line dimensions (e.g., space fill factor f described with respect to equations 10a and 10b), that space fill factor need not be strictly accurate, so long as a different space fill factor is used for each different base layer geometry.

Once the empirical grating factor lookup model has been finalized, measurement data is gathered from one or more patterned-based targets on a test sample having an unknown value(s) for the AOI(s) in "COLLECT MEASUREMENT DATA" step 330. The measured data is compared with the lookup model, which interpolates the data in the empirical lookup model for each wavelength and angle of incidence along the AOI(s) in a "SOLVE FOR ATTRIBUTE(S)" step 340-3.

Within step 340-3, an initial test value(s) for the AOI(s) is selected in a "SELECT AOI VALUE(S)" step 1041. Then, in "SELECT GC" step 1042, the set of grating factor values associated with the patterned base layer geometry of the measurement data is determined. Note that if only a single patterned base layer geometry is used, then step 1042 need not be performed.

Next, in a "GRATING FACTOR INTERPOLATION" step 1043, the set of grating factor values selected in step 1042 are interpolated along the AOI(s) to match the test AOI value(s) selected in step 1041, thereby generating a test grating factor(s) (as noted above, measurement data from a single target can be associated with multiple sets of grating factor values—e.g., grating factors $g_s$ and $g_p$ for p-polarized and s-polarized light, respectively). Note that while extrapolation could also be used to determine the test grating factor(s), extrapolation is inherently more prone to inaccuracy than interpolation.

Then, in a "MODELING" step 1044, the test grating factor value(s) and the test AOI value(s) are substituted back in to the adjusted model equation (s) used to determine the grating factor value(s) in step 1021. The resulting model output is compared to the actual measured data in a "MATCH?" step 1045. If the model output (based on the test AOI value(s) and the test grating factor(s)) is outside a predetermined tolerance band of the measured data, the process loops back to step 1041, where a new AOI value(s) is selected. Otherwise, the test AOI value(s) is provided as the output AOI value(s) for the test sample in "OUTPUT ATTRIBUTE VALUE(S)" step 350.

Figure 11A:
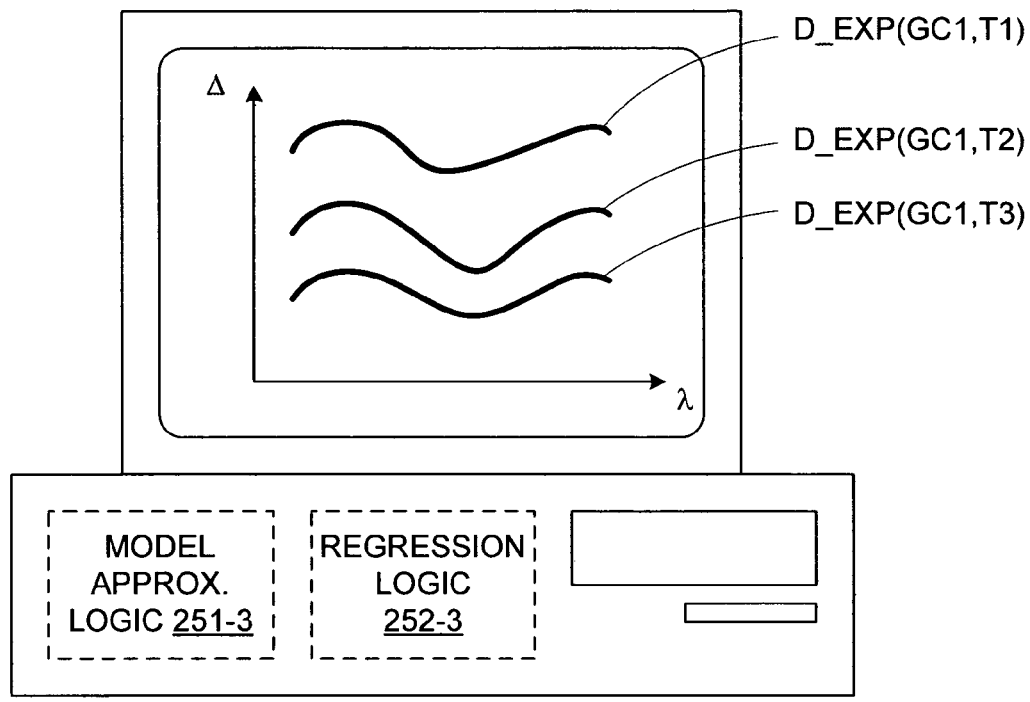
FIGS. 11A-11G depict a method for determining thin film attribute values using a grating factor lookup model, according to another embodiment of the invention.

FIGS. 11A-11G provide an exemplary depiction of the process described with respect to FIG. 10, according to an embodiment of the invention. In FIG. 11A (corresponding to step 310 of FIG. 10), data processing resources 250-3 gathers multiple experimental data sets D_EXP from patterned targets having different values of an AOI T (i.e., T1, T2, and T3).

Note that for exemplary purposes, FIGS. 11A-11G depict an operation based on a single AOI (thickness of a single thin film) and a single patterned base layer geometry (GC1).

However, as described above, the invention can be applied to systems involving multiple AOIs and multiple patterned base layer geometries. Note further that while a graph of delta ($\Delta$) versus wavelength ($\lambda$) is depicted for exemplary purposes, delta and wavelength could be replaced with any other optical metrology measurement parameters (e.g., reflectance and angle of incidence, respectively).

Figure 11B:
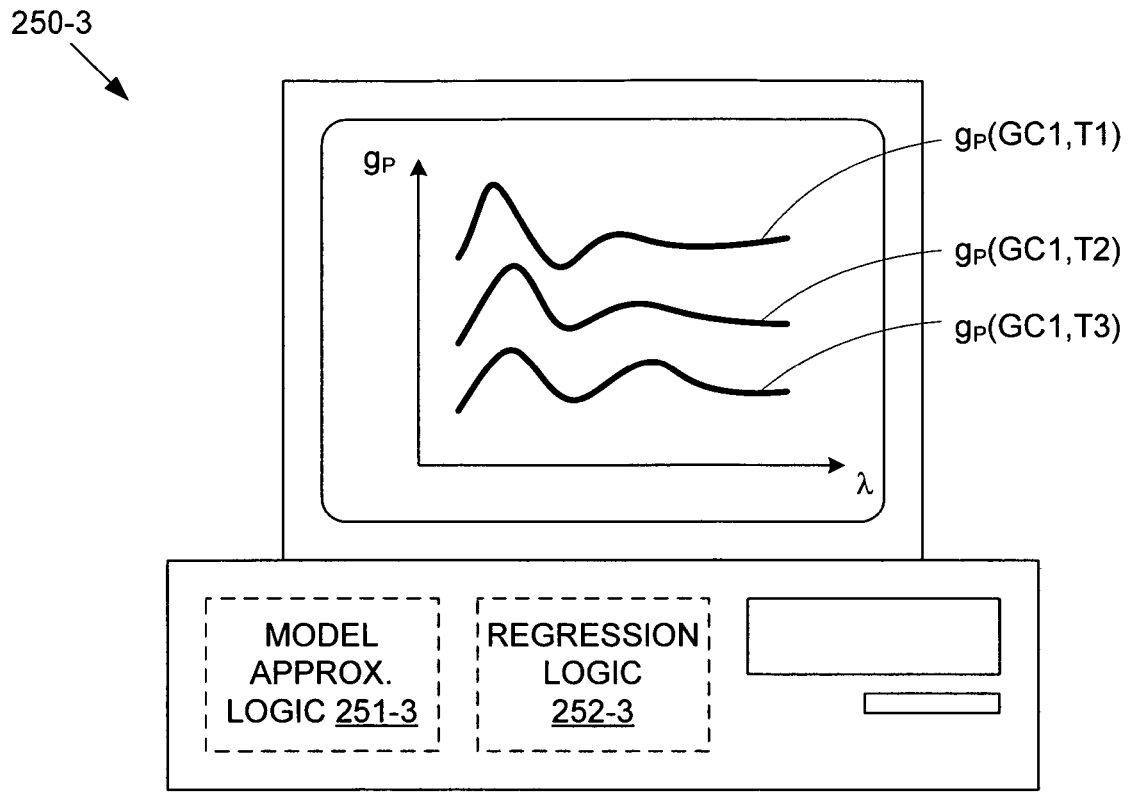
Figure 11C:
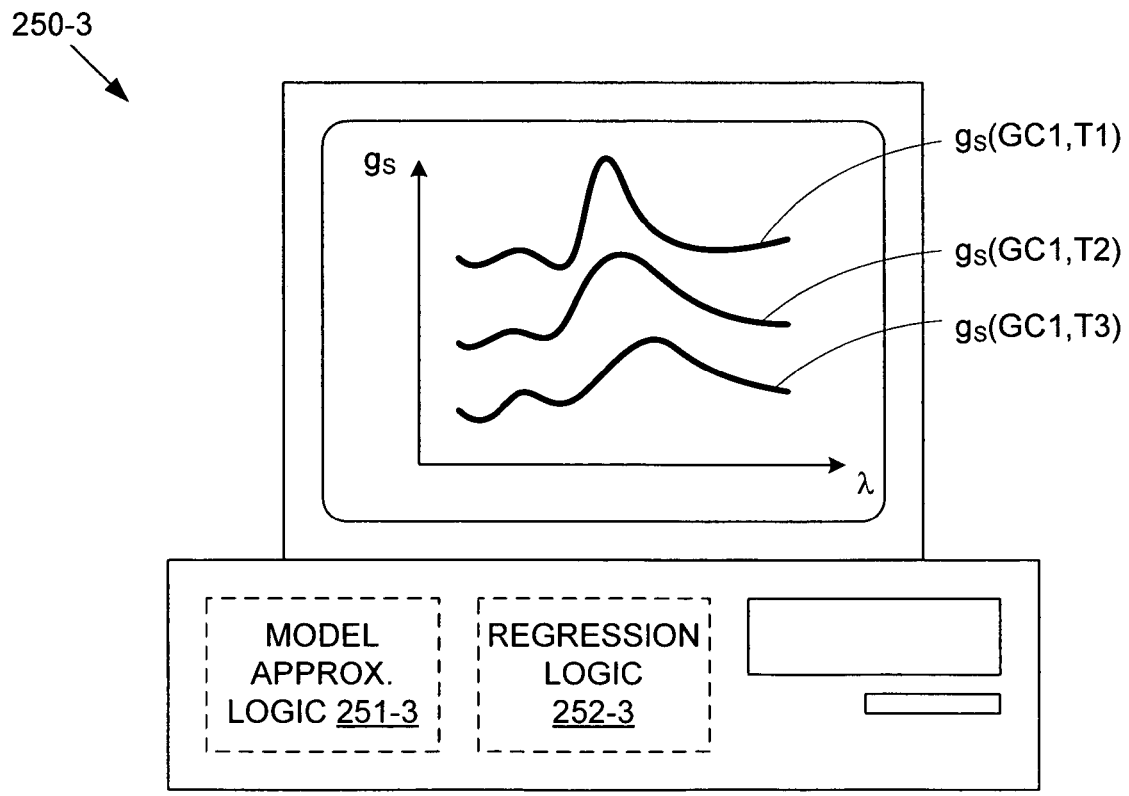

Model values for grating factors $g_p$ (i.e., $g_p$(GC1,T1), $g_p$(GC1,T2), $g_p$(GC1,T3)) and $g_s$ (i.e., $g_s$(GC1,T1), $g_s$(GC1,T2), $g_s$(GC1,T3)) are determined for data sets D_EXP(GC1,T1), D_EXP(GC1,T2), and D_EXP(GC1,T3) (step 1021), and are compiled into grating factor lookup models (step 1022) by model approximation logic 251-3, as shown in FIGS. 11B and 11C, respectively. As indicated in FIGS. 11B and 11C, the lookup model associates each set of grating factor values with a specific patterned base layer geometry (GC1) and an AOI value(s) (T1, T2, or T3).

Figure 11D:
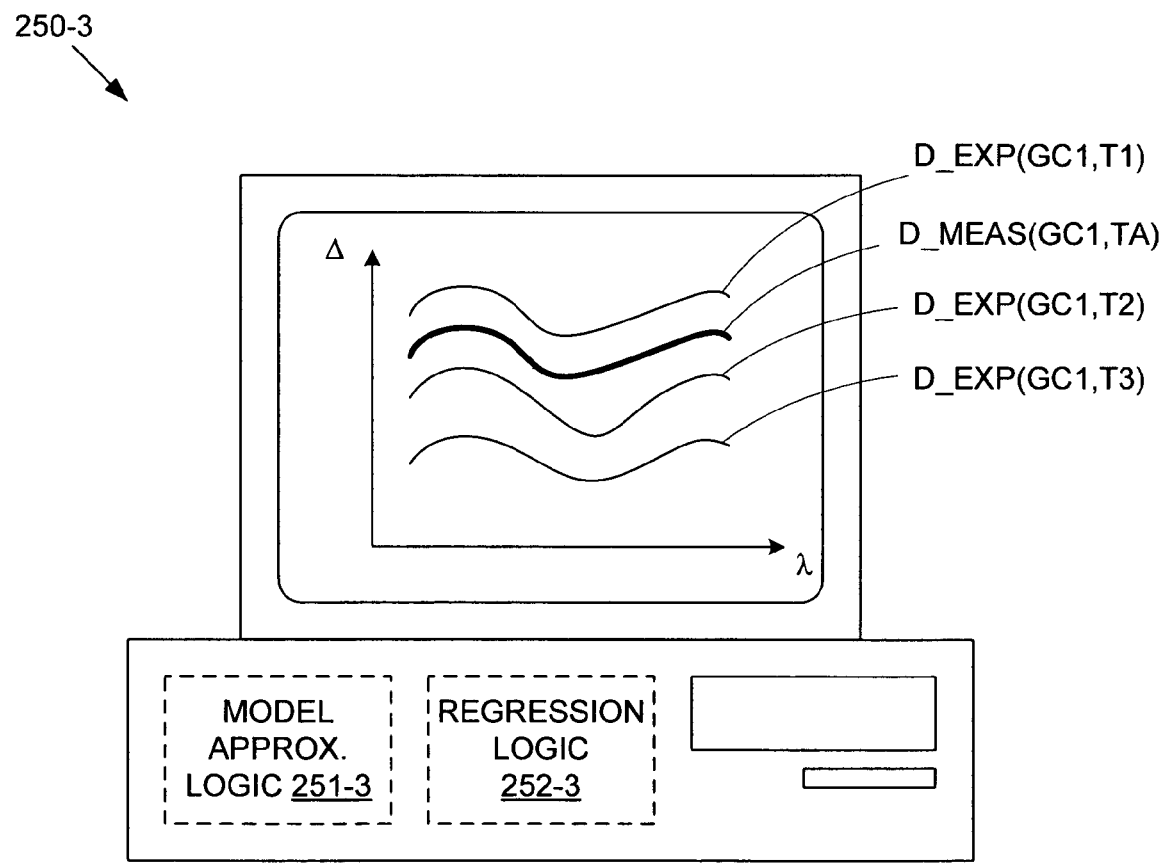

Then, in FIG. 11D, a new set of measurement data D_MEAS is taken from a new test sample (step 330). Measurement data D_MEAS is taken from a patterned target having an unknown AOI value (TA) and substantially the same geometry (GC1) as the patterned targets used to gather experimental data sets D_EXP(GC1,T1), D_EXP(GC1,T2), and D_EXP(GC1,T3) (shown for reference).

Figure 11E:
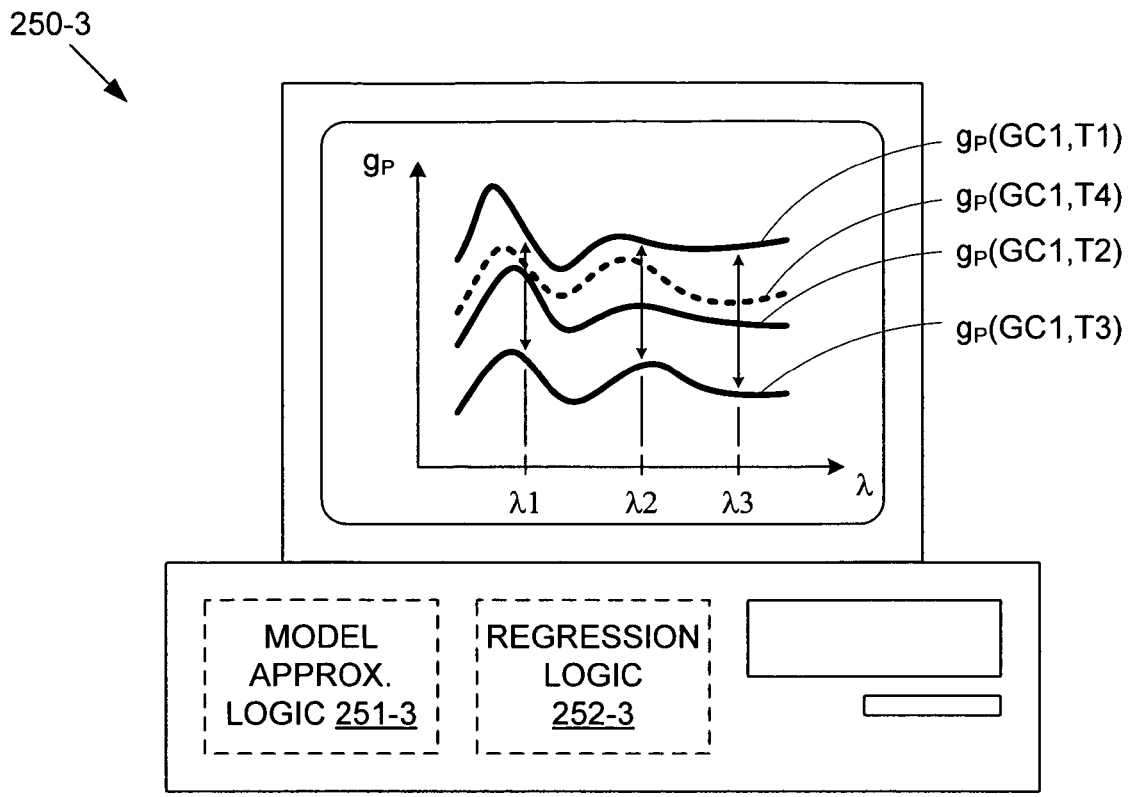
Figure 11F:
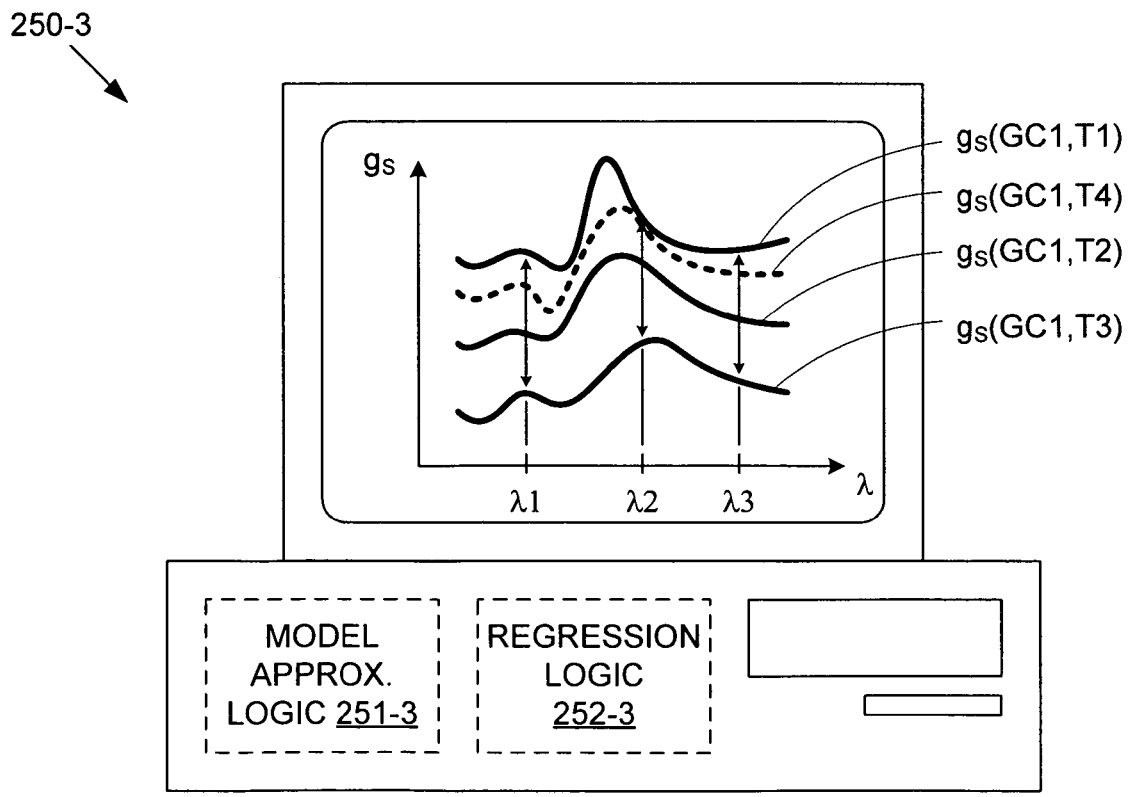

A test value T4 is selected for unknown AOI TA (step 1041), and the original model grating factor values $g_p$(GC1, T1)-$g_p$(GC1,T3) and $g_s$(GC1,T1)-$g_s$(GC1,T3) are interpolated (step 1043) along AOI T to derive test grating factors $g_p$(GC1,T4) and $g_s$(GC1,T4), respectively, that are associated with test value T4, as shown in FIGS. 11E and 11F, respectively. Note that since a single patterned base layer geometry is being used (GC1), optional step 1042 described with respect to FIG. 10 is not performed.

The interpolation (indicated by the vertical double-ended arrows) between model grating factor values $g_p$(GC1,T1)-$g_p$(GC1,T3) and between model grating factors $g_s$(GC1,T1)-$g_s$(GC1,T3) shown in FIGS. 11E and 11F, respectively, can be performed by regression logic 252-3 in an any manner. For example, cubic spline interpolation or quadratic interpolation could be used to define values for $g_p$(GC1,T4) and $g_s$(GC1,T4) at each wavelength λ (independent measurement parameter).

Figure 11G:
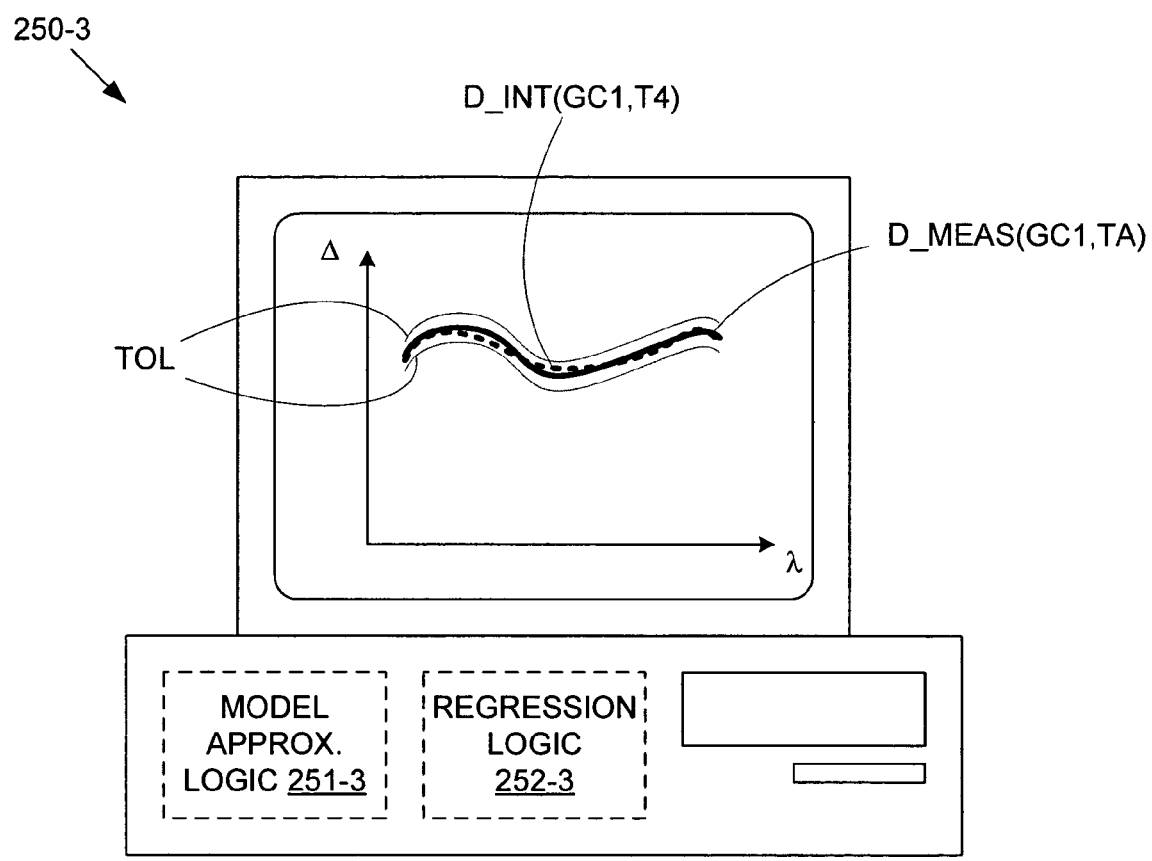

Grating factor values $g_p$(GC1,T4) and $g_s$(GC1,T4) are then substituted into the adjusted model equations (originally used to derive the grating factor lookup models) to generate a test model output D_INT(GC1,T4), shown in FIG. 11G (step 1044). Test model output D_INT(GC1,T4) is compared against the test sample measured data D_MEAS (GC1,TA) (step 1045), and if test model output D_INT (GC1,T4) is within a predetermined tolerance band TOL of measured data D_MEAS, AOI value T4 is output as the value for the test sample AOI TA (step 350). Otherwise, the process loops back to the selection of a new test value T4 and the generation of new test grating factors $g_p$(GC1,T4) and $g_s$(GC1,T4).

The various embodiments of the structures and methods of this invention that are described above are illustrative only of the principles of this invention and are not intended to limit the scope of the invention to the particular embodiments described. Thus, the invention is limited only by the following claims and their equivalents.

The invention claimed is:

1. A method for operating an optical metrology tool, the method comprising:
   collecting a first set of optical metrology data from a first patterned target, the first patterned target comprising a first set of one or more thin films on a first patterned layer;
   determining a first value set for one or more metrology attributes of the first set of one or more thin films;
   collecting a second set of optical metrology data from a second patterned target, the second patterned target comprising a second set of one or more thin films on a second patterned layer, the second patterned layer being substantially similar to the first patterned layer;
   determining a second value set for the one or more metrology attributes of the second set of one or more thin films;
   generating an empirical model using the first set of optical metrology data, the second set of optical metrology data, the first value set, and the second value set;
   collecting a third set of optical metrology data from a third patterned target on a first test sample, the third patterned target comprising a third set of one or more thin films on a third patterned layer, the third patterned layer being substantially similar to the first patterned layer;
   determining a third value set for the one or more metrology attributes of the third set of one or more thin films using the empirical model; and
   outputting the third value set as attribute values of the first test sample.

2. The method of claim 1, wherein generating the empirical model comprises:
   specifying a mathematical form for the empirical model, wherein the mathematical form comprises one or more model equations including a plurality of coefficients and one or more variables, wherein the one or more variables represent the one or more metrology attributes;
   substituting the first value set into the one or more variables to generate a first output from the one or more model equations;
   substituting the second value set into the one or more variables to generate a second output from the one or more model equations;
   generating a first set of coefficient values by regressing the one or more model equations along the coefficients until the first output and the second output are within a first predetermined tolerance band of the first set of optical metrology data and the second set of optical metrology data, respectively; and
   setting the plurality of coefficients in the one or more model equations equal to the first set of coefficient values.

3. The method of claim 2, wherein determining the third value set comprises regressing the empirical model along the one or more metrology attributes until an output of the empirical model is within a second tolerance band of the third set of optical metrology data.

4. The method of claim 3, wherein regressing the empirical model along the one or more metrology attributes further comprises regressing the empirical model along the plurality of coefficients.

5. The method of claim 1, wherein the empirical model comprises a lookup model correlating the first set of optical metrology data and the second set of optical metrology data with the first value set and the second value set, respectively.

6. The method of claim 5, wherein the first set of optical metrology data and the second set of optical metrology data are measured across a range of one or more independent measurement parameters, and
   wherein determining the third value set comprises regressing the lookup model along the one or more metrology attributes at a plurality of values in the range of the one or more independent measurement parameters.

7. The method of claim 1, wherein generating the empirical model comprises:
   specifying one or more model equations, wherein the one or more model equations comprise standard monolithic base layer model equations adjusted by one or more grating factors for compensating for patterned layer optical effects;
   solving the one or more model equations for the one or more grating factor variables using the first set of optical metrology data and the first value set to generate a first set of grating factor values;
   solving the one or more model equations for the one or more grating factor variables using the second set of optical metrology data and the second value set to generate a second set of grating factor values;
   creating a lookup model by associating the first set of grating factor values with the first attribute value and the first patterned layer, and by associating the second set of grating factor values with the second attribute value and the first patterned layer; and
   providing the lookup model as the empirical model.

8. The method of claim 7, wherein the empirical model comprises a first plurality of grating factor sets associated with the first patterned layer, the first plurality of grating factor sets including the first set of grating factor values and the second set of grating factor values, and wherein determining the third attribute value comprises:

selecting a test attribute value;

interpolating the first plurality of grating factor value sets along the one or more metrology attributes to derive a set of test grating factor values associated with the test attribute value;

substituting the set of test grating factor values and the test attribute value into the one or more model equations to generate a test output; and adjusting the test attribute value and repeating the steps of interpolating and substituting until the test output is within a predetermined tolerance band of the third set of optical metrology data; and providing the test attribute value as the third attribute value.

9. The method of claim 8, wherein the empirical model further comprises a second plurality of grating factor sets associated with a fourth patterned layer, and wherein the fourth patterned layer is different from the first patterned layer.

10. The method of claim 8, wherein the one or more model equations further comprise a space fill factor, wherein the empirical model further comprises a first value for the space fill factor associated with the first patterned layer, and wherein the empirical model further comprises a second value for the space fill factor associated with the fourth patterned layer.

11. The method of claim 7, wherein the one or more model equations comprise a plurality of recursive equations, wherein a first one of the plurality of recursive equations represents a monolithic layer on a grating layer, the grating layer comprising a plurality of grating lines separated by a filler material, and wherein the first one of the plurality of recursive equations comprises:

a first term comprising a first variable adjusted by a first one of the one or more grating factor variables, the first variable representing a first reflectance between the monolithic layer and one of the plurality of grating lines; and a second term comprising a second variable, the second variable representing a second reflectance between the monolithic layer and the filler material, wherein the first term and the second term are averaged according to a space fill factor representing a relative proportion between the plurality of grating lines and the filler material in the grating layer.

12. The method of claim 7, wherein the one or more model equations comprise a first set of recursive equations, wherein a first one of the first set of recursive equations represents a monolithic layer on a grating layer, the grating layer comprising a plurality of grating lines separated by a filler material, and wherein the first one of the first set of recursive equations comprises:

a first term comprising a first variable adjusted by a first one of the one or more grating factor variables, the first variable representing a first transmittance between the monolithic layer and one of the plurality of grating lines; and a second term comprising a second variable, the second variable representing a second transmittance between the monolithic layer and the filler material, wherein the first term and the second term are averaged according to a space fill factor representing a relative proportion between the plurality of grating lines and the filler material in the grating layer.

13. The method of claim 1, wherein determining the first value set comprises providing a first set of expected values for the first set of one or more thin films as the first value set, and wherein determining the second value set comprises defining a second set of expected values for the second set of one or more thin films as the second value set.

14. The method of claim 1, wherein the first patterned target is on a first wafer, wherein the first wafer further comprises a monolithic target, the monolithic target comprising the first set of one or more thin films on a monolithic layer, and wherein determining the first value set comprises measuring the one or more metrology attributes of the first set of one or more thin films at the monolithic target.

15. The method of claim 1, wherein the first set of optical metrology data and the second set of optical metrology data comprise a first set of ellipsometry data and a second set of ellipsometry data, respectively, at one or more wavelengths and at one or more angles of incidence.

16. The method of claim 1, wherein the first set of optical metrology data and the second set of optical metrology data comprise a first set of reflectometry data and a second set of reflectometry data, respectively, at one or more angles of incidence and at one or more wavelengths.

17. An optical metrology system comprising:

a beam source for generating a probe beam;

input optics for directing the probe beam at a test sample to generate a reflected beam;

output optics for directing a reflected beam at a detector for measuring the reflected beam; and model approximation logic for defining a set of model equations for one or more thin film layers on a patterned layer, the set of model equations comprising standard monolithic layer model equations adjusted by one or more grating factors compensating for patterned layer optical effects, for deriving a plurality of grating factor sets from a plurality of measurement data sets from the detector, and for generating an empirical model by associating each of the grating factor sets with one or more metrology attribute values from a corresponding one of the plurality of measurement data sets.

18. The optical metrology system of claim 17, further comprising regression logic for selecting a test value set for the one or more metrology attributes of a test measurement data set from the detector, for interpolating the plurality of grating factor along the one or more metrology attribute values sets to generate a test grating factor set corresponding to the test value set, for applying the test grating factor set and the test value set to the set of model equations to generate a test output, for adjusting the test value set until the test output is within a predetermined tolerance band of the test measurement data set, and for providing the test value set as an output value set for the test measurement data set.

19. The optical metrology system of claim 18, wherein the optical metrology system comprises an ellipsometry system.

20. The optical metrology system of claim 18, wherein the optical metrology system comprises a reflectometry system.

21. A method for performing an optical metrology measurement, the method comprising:

gathering a plurality of reference data sets of optical metrology measurement data from a plurality of reference patterned targets;

specifying a reference attribute value set for one or more optical metrology attributes for each of the plurality of reference patterned targets;

generating an empirical patterned target model using the plurality of reference data sets and each reference attribute value set;

gathering a test data set of optical metrology measurement data from a test patterned target;

applying the test data set to the empirical patterned target model to generate an output value set for the one or more optical metrology attributes for the test patterned target; and providing an output including the output value set.

22. The method of claim 21, wherein generating the empirical patterned target model comprises:

defining a set of model equations, the set of model equations comprising a set of standard monolithic layer model equations adjusted by one or more grating factors to compensate for patterned layer optical effects;

deriving a grating factor value set for each of the reference data sets by substituting the reference data set and the reference attribute value set associated with the reference data set into the set of model equations and solving for the one or more grating factors;

compiling a grating factor lookup model by associating each grating factor value set with the reference attribute value set used in the derivation of the grating factor value set, and by associating each grating factor value set with a reference patterned layer geometry of the one of the plurality of reference patterned targets providing the reference data set used in the derivation of the grating factor value set.

23. The method of claim 22, wherein applying the empirical patterned target model to the test data set comprises:

specifying a test attribute value set for the one or more metrology attributes of the test patterned target;

grouping all the grating factor value sets associated with the reference patterned layer geometry substantially similar to a test patterned layer geometry of the test patterned target into a grating factor grouping;

interpolating the grating factor value sets in the grating factor grouping along the one or more optical metrology attributes to generate a test grating factor value set corresponding to the test attribute value set;

generating a test model output by substituting the test grating factor value set and the test attribute value set into the set of model equations;

adjusting the test attribute value set and repeating the steps of interpolating and generating until the test model output is within a predetermined tolerance band of the test data set; and providing the test attribute value set as an output value set for the one or more metrology attributes of the test patterned target.

24. The method of claim 21, specifying the reference attribute value set comprises specifying expected values for the one or more optical metrology attributes.

25. The method of claim 21, wherein each of the plurality of reference patterned targets comprises at least one thin film layer formed on a patterned layer, and wherein specifying the reference attribute value set comprises:

measuring a monolithic value set for the one or more optical metrology attributes of a plurality of monolithic targets, each of the plurality of monolithic targets comprising the at least one thin film layer of an adjacent one of the plurality of reference patterned targets formed on a monolithic layer; and providing the monolithic value set of each of the plurality of monolithic targets as the reference attribute value set of the adjacent one of the plurality of reference patterned targets.

26. A method for operating a plurality of metrology tools, the method comprising:

measuring a target location on a test sample using each of the plurality of metrology tools to generate a plurality of metrology data sets;

compiling the plurality of metrology data sets into a single empirical model for the plurality of metrology tools, the single empirical model being a selected model equation form;

measuring attributes of a thin film formed on a patterned base layer using the single empirical model; and outputting the attributes of the thin film.

27. A method for creating a model, the method comprising:

collecting a first set of optical metrology data from a first patterned target, the first patterned target comprising a first set of one or more thin films on a first patterned layer;

determining a first value set for one or more metrology attributes of the first set of one or more thin films;

collecting a second set of optical metrology data from a second patterned target, the second patterned target comprising a second set of one or more thin films on a second patterned layer, the second patterned layer being substantially similar to the first patterned layer;

determining a second value set for the one or more metrology attributes of the second set of one or more thin films;

generating an empirical model using the first set of optical metrology data, the second set of optical metrology data, the first value set, and the second value set; and outputting the empirical model.

28. The method of claim 27, wherein generating the empirical model comprises:

specifying a mathematical form for the empirical model, wherein the mathematical form comprises one or more model equations including a plurality of coefficients and one or more variables, wherein the one or more variables represent the one or more metrology attributes;

substituting the first value set into the one or more variables to generate a first output from the one or more model equations;

substituting the second value set into the one or more variables to generate a second output from the one or more model equations;

generating a first set of coefficient values by regressing the one or more model equations along the coefficients until the first output and the second output are within a first predetermined tolerance band of the first set of optical metrology data and the second set of optical metrology data, respectively; and setting the plurality of coefficients in the one or more model equations equal to the first set of coefficient values.

29. The method of claim 27, wherein the empirical model comprises a lookup model correlating the first set of optical metrology data and the second set of optical metrology data with the first value set and the second value set, respectively.

30. The method of claim 29, wherein the first set of optical metrology data and the second set of optical metrology data are measured across a range of one or more independent measurement parameters.

31. The method of claim 27, wherein generating the empirical model comprises:

specifying one or more model equations, wherein the one or more model equations comprise standard monolithic base layer model equations adjusted by one or more grating factors for compensating for patterned layer optical effects;

solving the one or more model equations for the one or more grating factor variables using the first set of optical metrology data and the first value set to generate a first set of grating factor values;

solving the one or more model equations for the one or more grating factor variables using the second set of optical metrology data and the second value set to generate a second set of grating factor values;

creating a lookup model by associating the first set of grating factor values with the first attribute value and the first patterned layer, and by associating the second set of grating factor values with the second attribute value and the first patterned layer; and providing the lookup model as the empirical model.

32. The method of claim 31, wherein the empirical model comprises a first plurality of grating factor sets associated with the first patterned layer, the first plurality of grating factor sets including the first set of grating factor values and the second set of grating factor values.

33. The method of claim 31, wherein the one or more model equations comprise a plurality of recursive equations, wherein a first one of the plurality of recursive equations represents a monolithic layer on a grating layer, the grating layer comprising a plurality of grating lines separated by a filler material, and wherein the first one of the plurality of recursive equations comprises:

a first term comprising a first variable adjusted by a first one of the one or more grating factor variables, the first variable representing a first reflectance between the monolithic layer and one of the plurality of grating lines; and a second term comprising a second variable, the second variable representing a second reflectance between the monolithic layer and the filler material, wherein the first term and the second term are averaged according to a space fill factor representing a relative proportion between the plurality of grating lines and the filler material in the grating layer.

34. The method of claim 31, wherein the one or more model equations comprise a first set of recursive equations, wherein a first one of the first set of recursive equations represents a monolithic layer on a grating layer, the grating layer comprising a plurality of grating lines separated by a filler material, and wherein the first one of the first set of recursive equations comprises:

a first term comprising a first variable adjusted by a first one of the one or more grating factor variables, the first variable representing a first transmittance between the monolithic layer and one of the plurality of grating lines; and a second term comprising a second variable, the second variable representing a second transmittance between the monolithic layer and the filler material, wherein the first term and the second term are averaged according to a space fill factor representing a relative proportion between the plurality of grating lines and the filler material in the grating layer.

35. The method of claim 27, wherein determining the first value set comprises providing a first set of expected values for the first set of one or more thin films as the first value set, and wherein determining the second value set comprises defining a second set of expected values for the second set of one or more thin films as the second value set.

36. The method of claim 27, wherein the first patterned target is on a first wafer, wherein the first wafer further comprises a monolithic target, the monolithic target comprising the first set of one or more thin films on a monolithic layer, and wherein determining the first value set comprises measuring the one or more metrology attributes of the first set of one or more thin films at the monolithic target.

37. The method of claim 27, wherein the first set of optical metrology data and the second set of optical metrology data comprise a first set of ellipsometry data and a second set of ellipsometry data, respectively, at one or more wavelengths and at one or more angles of incidence.

38. The method of claim 27, wherein the first set of optical metrology data and the second set of optical metrology data comprise a first set of reflectometry data and a second set of reflectometry data, respectively, at one or more angles of incidence and at one or more wavelengths.

39. A method for creating a model, the method comprising:

gathering a plurality of reference data sets of optical metrology measurement data from a plurality of reference patterned targets;

specifying a reference attribute value set for one or more optical metrology attributes for each of the plurality of reference patterned targets;

generating an empirical patterned target model using the plurality of reference data sets and each reference attribute value set; and outputting the empirical patterned target model.

40. The method of claim 39, wherein generating the empirical patterned target model comprises:

defining a set of model equations, the set of model equations comprising a set of standard monolithic layer model equations adjusted by one or more grating factors to compensate for patterned layer optical effects;

deriving a grating factor value set for each of the reference data sets by substituting the reference data set and the reference attribute value set associated with the reference data set into the set of model equations and solving for the one or more grating factors; and compiling a grating factor lookup model by associating each grating factor value set with the reference attribute value set used in the derivation of the grating factor value set, and by associating each grating factor value set with a reference patterned layer geometry of the one of the plurality of reference patterned targets providing the reference data set used in the derivation of the grating factor value set.

41. The method of claim 39, wherein specifying the reference attribute value set comprises specifying expected values for the one or more optical metrology attributes.

42. The method of claim 39, wherein each of the plurality of reference patterned targets comprises at least one thin film layer formed on a patterned layer, and wherein specifying the reference attribute value set comprises:

measuring a monolithic value set for the one or more optical metrology attributes of a plurality of monolithic targets, each of the plurality of monolithic targets comprising the at least one thin film layer of an adjacent one of the plurality of reference patterned targets formed on a monolithic layer; and providing the monolithic value set of each of the plurality of monolithic targets as the reference attribute value set of the adjacent one of the plurality of reference patterned targets.

* * * * *